(12) United States Patent
Sweeney et al.

(10) Patent No.: US 8,846,764 B2
(45) Date of Patent: Sep. 30, 2014

(54) METHODS OF MODULATING CELL PROLIFERATION AND CYST FORMATION IN POLYCYSTIC KIDNEY AND LIVER DISEASES

(75) Inventors: William E. Sweeney, Waukesha, WI (US); Ellis D. Avner, Milwaukee, WI (US); Richard J. Roman, Brookfield, WI (US)

(73) Assignee: The Medical College of Wisconsin, Inc., Milwaukee, WI (US)

(*) Notice: Subject to any disclaimer, the term of this patent is extended or adjusted under 35 U.S.C. 154(b) by 1416 days.

(21) Appl. No.: 11/900,722

(22) Filed: Sep. 13, 2007

(65) Prior Publication Data
US 2008/0167382 A1    Jul. 10, 2008

Related U.S. Application Data

(60) Provisional application No. 60/844,218, filed on Sep. 13, 2006.

(51) Int. Cl.

| | | |
|---|---|---|
| A61K 31/155 | (2006.01) | |
| A61K 31/535 | (2006.01) | |
| A61K 31/4406 | (2006.01) | |
| A61K 31/415 | (2006.01) | |
| A61K 31/4155 | (2006.01) | |
| A61K 31/4164 | (2006.01) | |
| A61K 31/421 | (2006.01) | |

(52) U.S. Cl.
USPC ........ 514/633; 514/238.2; 514/352; 514/399; 514/406; 514/378

(58) Field of Classification Search
USPC .............. 514/633, 238.2, 352, 399, 406, 378
See application file for complete search history.

(56) References Cited

U.S. PATENT DOCUMENTS

| | | |
|---|---|---|
| 6,395,781 B1 | 5/2002 | Roman |
| 6,818,662 B2 | 11/2004 | Ito et al. |
| 6,864,254 B1 | 3/2005 | Sato et al. |
| 7,078,400 B2 | 7/2006 | Sato et al. |
| 7,214,714 B2 | 5/2007 | Sato et al. |
| 2003/0114513 A1 | 6/2003 | Jensen et al. |
| 2004/0110830 A1 | 6/2004 | Sato et al. |
| 2005/0124618 A1 | 6/2005 | Roman et al. |

FOREIGN PATENT DOCUMENTS

| | | |
|---|---|---|
| EP | 1226819 A1 | 7/2002 |
| EP | 1389611 A1 | 2/2004 |
| WO | 1997035601 A1 | 10/1997 |
| WO | 2006073572 A2 | 7/2006 |

OTHER PUBLICATIONS

STN RN 339068-25-6; 2001; accessed Mar. 17, 2010.*
Torres et al.; "Epidermal growth factor receptor tyrosine kinase inhibition is not protective in PCK rats"; 2004; Kidney International; 66: 1766-1773.*
McGrawth-Morrow et al.; "VEGF receptor 2 blockade leads to renal cyst formation in mice"; 2006; Kidney International; 69: 1741-1748.*
Nakamura T et al., Pyrazole derivatives as new potent and selective 20-hydroxy-5, 8, 11, 14-eicosatetraenoic acid synthase inhibitors, Bioorg Med Chem. 12:6209-6219, 2004.
Nakamura T et al., Imidazole derivatives as new potent and selective 20-HETE synthase inhibitors, Bioorg Med Chem Lett. 14:333-336, 2004.
Nakamura T et al., Pyrazole and isoxazole derivatives as new, potent, and selective 20-hydroxy-5, 8, 11, 14-eicosatetraenoic acid synthase inhibitors, J Med Chem. 46:5416-5427, 2003.
Nakamura T et al., Design and Synthesis of 1-(4-benzoylphenyl)imidazole derivatives as new potent 20-HETE synthase inhibitors, Bioorg Med Chem Lett. 14:5305-5308, 2004.
Sato M et al., Discovery of a N'-hydroxyphenylformamadine derivitive HET0016 as a potent and selective 20-HETE synthase inhibitor, Bioorg Med Chem Lett. 11:2993-2995, 2001.
Miyata N et al., HET0016, a potent and selective inhibitor of 20-HETE synthesizing enzyme, Br J Pharmacol. 133:325-329, 2001.
Xu F et al., Antihypertensive effect of mechanism-based inhibition of renal arachidonic acid w-hydroxylase activity, Am J Physiol Regul Integr Comp Physiol 283:R710-720, 2002.
Yu M et al., Effects of a 20-HETE antagonist and agonists on cerebral vascular tone, Eur J Pharmacol. 486:297-306, 2004.
Yu M et al., 20-hydroxyeicosatetraenoic acid (20-HETE): structural determinants for renal vasoconstriction, Bioorg Med Chem. 11:2803-2821, 2003.
Alonso-Galicia M et al., 20-HETE agonists and antagonists in the renal circulation, Am J Physiol. 277:F790-796, 1999.
Nakamura et al., Pyrazole derivatives as new potent and selective 20-hydroxy-5,8,11,14-eicosatetraenoic acid synthase inhibitors, Bioorganic & Medicinal Chemistry, vol. 12, No. 23, Dec. 1, 2004, pp. 6209-6219.
Nakamura et al., Design and synthesis of 1-(4-benzoylphenyl)imidazole derivatives as new potent 20-HETE synthase inhibitors, Bioorganic & Medicinal Chemistry Letters, vol. 14, No. 21, Nov. 1, 2004, pp. 5305-5308.

(Continued)

*Primary Examiner* — Timothy Thomas
(74) *Attorney, Agent, or Firm* — Quarles & Brady LLP

(57) ABSTRACT

The present invention provides a method for preferentially reducing the proliferation of cystic epithelial cells in the kidney or bile duct in a mammal in need thereof by administering a 20-HETE synthesizing enzyme inhibitor or a 20-HETE antagonist to the mammal in an amount sufficient to preferentially reduce the proliferation of cystic epithelial cells over normal epithelial cells such as tubule epithelial cells in the kidney or bile duct. The present invention also provides a method for preventing or treating autosomal dominant polycystic kidney disease (ADPKD), autosomal recessive polycystic kidney disease (ARPKD), ARPKD associated congenital hepatic fibrosis, ARPKD associated Caroli's disease, or cholangiocarcinoma in a mammal in need thereof by administering a 20-HETE synthesizing enzyme inhibitor or a 20-HETE antagonist to the mammal in an amount sufficient to prevent or treat the disease.

13 Claims, 12 Drawing Sheets
(5 of 12 Drawing Sheet(s) Filed in Color)

(56) References Cited

OTHER PUBLICATIONS

Hoagland et al., Inhibitors of Renal 20-HETE Formation Promotes Salt-Sensitive Hypertension in Rats, Hypertension 42:669-673, 2003.

Roman et al., Characterization of Blood Pressure and Renal Function in Chromosome 5 Congenic Strains of Dahl S Rats, Am. J. Physiol. 290:F1463-71, 2006.

Nakagawa et al., Salt-Sensitive Hypertension is Associated with Dysfunctional Cyp4a10 Gene and Kidney Epithelial Sodium Channel, J. Clin. Invest. 116(6):1696-702, Jun. 2006.

Chen et al., Transfection of an Active Cytochrome P450 Arachidonic Acid Epoxygenase Indicates that 14,15-Epoxyeicosatrienoic Acid Functions as an Intracellular Second Messenger in Response to Epidermal Growth Factor, J. Biol. Chem. 274(8):4764-9, Feb. 1999.

Lin et al., 20-Hydroeicosatetraenoic Acid is Formed in Response to EGF and is a Mitogen in Rat Proximal Tubule, AJP—Renal Physiology, 269:6 806-F816, 1995.

Guo et al., "Human U251 glioma cell proliferation is suppressed by HET0016 [N-hydroxy-N'-(4-butyl-2-methylphenyl) formamidine], a selective inhibitor of CYP4A", J Pharmacol Exp Ther, 2005; 315:526-533.

Wilson et al., "Polycystic kidney disease", N Engl J Med, 2004; 350:151-164.

Sweeney et al. "Treatment of polycystic kidney disease with a novel tyrosine kinase inhibitor", Kidney Int, 2000; 57:33-40.

* cited by examiner

METHODS OF MODULATING CELL PROLIFERATION AND CYST FORMATION IN POLYCYSTIC KIDNEY AND LIVER DISEASES

CROSS-REFERENCE TO RELATED APPLICATIONS

This application claims the benefit of U.S. provisional application Ser. No. 60/844,218, filed on Sep. 13, 2006, which is herein incorporated by reference in its entirety.

STATEMENT REGARDING FEDERALLY SPONSORED RESEARCH OR DEVELOPMENT

This invention was made with United States government support awarded by the following agencies: NIH P50-DK57306 and R37-HL36279. The United States government has certain rights in this invention.

BACKGROUND OF THE INVENTION

Renal cystic diseases (RCD) include a group of monogenic kidney abnormalities which cause significant morbidity and mortality (Dell, K., et al., Polycystic kidney disease, in Pediatric Nephrology, E. D. Avner, W. E. Harmon, and P. Niaudet, Editors. 2004, Lippincott Williams & Wilkins: Philadelphia. p. 675-699). Histopathologically, renal cysts are fluid filled, epithelia lined, dilated saccular lesions which generally arise from tubular segments. The most common cause of nondysplastic, nonsyndromal multiple renal cysts are autosomal dominant polycystic kidney disease (ADPKD) (MIM 601313 and MIM 173910) (PKD1 and PKD2) and autosomal recessive polycystic kidney disease (ARPKD) (MIM 263200) (PKHD1).

ADPKD is the most common renal monogenic disease with an incidence of about 1 in 500. ADPKD comprises 5-8% of all individuals requiring renal replacement therapy (dialysis and/or kidney transplantation). Approximately 80-85% of ADPKD patients have inherited mutations in the PKD1 gene, located on chromosome 16p13, which encodes for the protein called polycystin-1 (PC-1). The remaining 10-15% of ADPKD cases have mutations in the PKD2 gene located on chromosome 4q21, which encodes for polycystin-2 (PC-2). ADPKD is usually asymptomatic until the middle decades of life because the kidney has reserve function and only 10-15% of health renal mass is needed to sustain life. However, with time renal function in individuals with ADPKD gradually deteriorates as the kidneys become replaced by multitudes of fluid-filled cysts. Eventually the damage to the remaining portions of the kidney becomes so severe that renal replacement therapy becomes necessary. It should also be mentioned that 2-5% of ADPKD patients present with a severe neonatal course and exhibit significant morbidity and mortality in childhood.

ARPKD caused by mutations on PKHD1 is a significant cause of renal and bile duct-related morbidity and mortality in childhood. Estimates of disease prevalence vary widely but an overall frequency of 1 in 20,000 live births and a carrier level up to 1:70 have been recently proposed (Zerres, K., et al., Prenatal diagnosis of autosomal recessive polycystic kidney disease (ARPKD): Molecular genetics, clinical experience, and fetal morphology. Am J Med Genet, 1998. 76: p. 137-144). Liver disease is invariably present in all ARPKD patients (Dell, K., et al., Polycystic kidney disease, in Pediatric Nephrology, E. D. Avner, W. E. Harmon, and P. Niaudet, Editors. 2004, Lippincott Williams & Wilkins: Philadelphia. p. 675-699). The chief pathologic hallmarks of ARPKD associated liver disease are hepatic lesions of biliary dysgenesis due to ductal plate malformation and associated periportal fibrosis resulting in congenital hepatic fibrosis (CHF) and dilatation of intrahepatic bile ducts (Caroli's disease) (Blyth, H. and B. G. Ockenden, J Med Genet, 1971, 8:257-284; Jorgensen, M. J., Acta Pathol Microbiol Scand Suppl, 1977, 257:1-87; Desmet, V. J., Hepatology, 1992, 16:1069-83; Dell, K. and E. Avner. Autosomal recessive polycystic kidney disease. GeneReviews; Genetic Disease Online Reviews at Gene Tests-GeneClinics 2003; Davis, I. D., et al., Pediatr Transplant, 2003, 7:364-9; and Harris, P. C. and S. Rossetti, Mol Genet Metab, 2004, 81:75-85). All patients with CHF have a mutation in the ARPKD gene, PKHD1. The biliary proliferation associated with ARPKD may also lead to cholangiocarcinoma.

Although the mutated genes that cause PKD were identified years ago, the pathway(s) leading from the mutated proteins to the formation of cysts remain unknown and are the subject of intense investigation. Over the years, it has become apparent that the PKD (PKD1, PKD2 and PKHD1) proteins are involved in the transduction of environmental cues into appropriate cellular responses. The expression in of PKD proteins in cilia, basal bodies, intercellular junctions, and at the focal adhesions suggests that there may be common signaling pathways for cyst formation, through the abnormal integration of signal transduction pathways (Wilson P. D., N Engl J Med, 2004, 350:151-64; Nauli S. M. et al., Nat Genet, 2003, 33:129-37).

PKD cystic renal epithelia share common phenotypic abnormalities despite the different genetic mutations that underlie the disease. Numerous animal models as well as in vitro cell culture systems utilizing cells derived from cysts obtained from human and animal models have established that the development of PKD is characterized by a switch from a well-differentiated, nonproliferative, reabsorptive epithelia to a partially dedifferentiated, secretory epithelia characterized by polarization defects and high rates of proliferation and apoptosis (Dell, K., et al., Polycystic kidney disease, in Pediatric Nephrology, E. D. Avner, W. E. Harmon, and P. Niaudet, Editors. 2004, Lippincott Williams & Wilkins: Philadelphia. p. 675-699; Wilson P. D., N Engl J Med, 2004. 350:151-64; Wilson P. D., Int J Biochem Cell Biol, 2004, 36:1868-73; Murcia N. S. et al., Kidney Int, 1999, 55:1187-1197; Harris P. C. and S. Rossetti, Mol Genet Metab, 2004, 81:75-85). It is clear that the development and progressive enlargement of cysts require proliferation of the tubular epithelial cells, transepithelial fluid secretion, and extracellular matrix remodeling (Welling, L. W. and J. J. Grantham, Cystic and developmental diseases of the kidney, in The Kidney, B. M. R. Brenner, F. C., Editor. 1991, WB Saunders: Philadelphia. p. 1657-1694; and Grantham J. J., AM J Kidney Dis, 1996, 28:788-803). Indeed, since the first anatomical studies performed in the 19$^{th}$ century, proliferation has been recognized as the hallmark of cystic epithelia. Cultured epithelial cells from patients or animal models of PKD have consistently demonstrated an increased intrinsic capacity for proliferation and survival (Gabow P. A., N Engl J Med, 1993, 329:332-42; Wilson P. D., N Engl J Med, 2004, 350:151-64; Grantham J. J., AM J Kidney Dis, 1996, 28:788-803; Grantham J. J. et al., Kidney Int, 1987, 31:1145-1152).

BRIEF SUMMARY OF THE INVENTION

The present invention provides a method for preferentially reducing the proliferation of cystic epithelial cells in the kidney or bile duct in a mammal (e.g., a human subject, a mouse, or a rat). The method includes the step of administering a 20-HETE synthesizing enzyme inhibitor or a 20-HETE antagonist to the mammal in need thereof in an amount sufficient to preferentially reduce the proliferation of cystic epithelial cells over normal epithelial cells such as tubule epithelial cells in the kidney or bile duct.

The present invention also provides a method for preventing or treating ADPKD, ARPKD, ARPKD associated CHF, ARPKD associated Caroli's disease, or cholangiocarcinoma in a mammal (e.g., a human subject, a mouse, or a rat). The method includes the step of administering a 20-HETE synthesizing enzyme inhibitor or a 20-HETE antagonist to the mammal in need thereof in an amount sufficient to prevent or treat the disease.

BRIEF DESCRIPTION OF THE SEVERAL VIEWS OF THE DRAWINGS

The patent or application file contains at least one drawing executed in color. Copies of this patent or patent application publication with color drawings will be provided by the Office upon request and payment of the necessary fee.

DETAILED DESCRIPTION OF THE INVENTION

Figure 1:
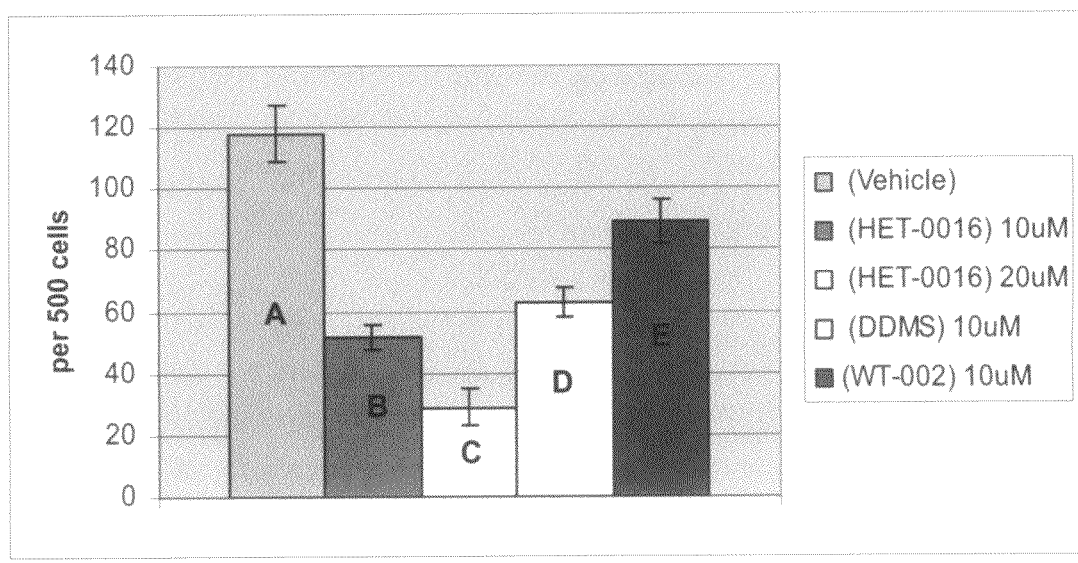
FIG. 1 shows the effect of N-hydroxy-N'-(4-n-butyl-2-methylphenyl)-formamidine (HET0016, a selective inhibitor of the formation of 20-HETE), dibromododecenyl methylsulfonimide (DDMS, a chemically dissimilar inhibitor of 20-HETE from HET0016), and 20-hydroxyeicosa-6(Z),15 (Z)-dienoic acid (WIT-002, a 20-HETE receptor antagonist) on the proliferation of cystic renal epithelial cells (REC11) derived from a BPK mouse model of ARPKD.

It is disclosed here that inhibiting the activity of 20-HETE can selectively reduce the proliferation of cystic epithelial cells in the kidney or bile duct versus the corresponding normal cells. In one aspect, the present invention relates to a method for preferentially reducing the proliferation of cystic epithelial cells in the kidney or bile duct in a mammal by administering a 20-HETE synthesizing enzyme inhibitor or a 20-HETE antagonist to the mammal (e.g., a human subject, a mouse, or a rat) in need thereof in an amount sufficient to preferentially reduce the proliferation of cystic epithelial cells over normal epithelial cells such as tubule epithelial cells in the kidney or bile duct.

In another aspect, the present invention relates to a method for preventing or treating ADPKD, ARPKD, ARPKD associated CHF, ARPKD associated Caroli's disease, or cholangiocarcinoma in a mammal (e.g., a human subject, a mouse, or a rat) by administering a 20-HETE synthesizing enzyme inhibitor or a 20-HETE antagonist to the mammal in need thereof in an amount sufficient to prevent or treat the disease. By preventing the disease, we mean preventing the development of the disease or reducing the severity of the disease at its onset. Improvements resulted from the treatment may be observed by both noninvasive (indirect) and invasive (tissue examination) methods. For kidney, noninvasive tests demonstrating a positive response to therapy include increased maximal urinary concentrating ability (e.g., by measuring urinary osmolality after 8 hours of water deprivation and administration of 10-20 mcg of vasopressin intranasally), stabilization or decrease in serum creatinine, stable or increased glomerular filtration rate (GFR) calculated based on serum creatinine level by formulas which adjust for patient height (see e.g., Schwartz G J et al., Pediatr Clin North Am, 1987, 34:571), improvement in hypertension (e.g., decreased blood pressure or use of fewer antihypertensive medications to maintain blood pressure control), and decrease in overall kidney size (may be monitored by, e.g., ultrasound or magnetic resonance imaging: see e.g., Torres V. E. et al. Clin J Am Soc Nephrol, 2007, 2:112-20; and Grantham J. J. et al. Clin J Am Soc Nephrol, 2007, 1:148-57). Invasive tests include kidney biopsy with evaluation of renal morphometric cystic index and morphometric assessment of the degree of tubulointerstitial fibrosis (see e.g., Sweeney W W et al., Kidney Inter, 64:1310-1319, 2003). For biliary lesions, noninvasive tests demonstrating a positive response to therapy include decrease in spleen size (may be monitored by, e.g., ultrasound or magnetic resonance imaging), decrease in degree of portal hypertension (may be monitored by, e.g., ultrasound or magnetic resonance imaging and associated flow studies), improvement by MRI-ERCP (Magnetic Resonance Imaging-Endoscopic Retrograde Cholangiopancreatography) which is indicated by a decrease in overall portal ductal ectasia, and increased MR-elastography (a measurement of organ fibrosis by MRI: see e.g., Yin M et al., Magn Reson Med, 2007, 58:346-353). Invasive tests include liver biopsy for morphological assessment of biliary ductal ectasia and peri-portal fibrosis. In the case of cholangiocarcinoma treatment, the size of the tumor may be monitored. A reduction in the size of the tumor indicates an improvement.

ADPKD and ARPKD cystic renal epithelia share common phenotypic abnormalities despite the different genetic mutations that underlie the disease. Numerous animal models as well as in vitro cell culture systems utilizing cells derived from cysts obtained from human and animal models have established that the development of PKD is characterized by a switch from a well-differentiated, nonproliferative, reabsorptive epithelia to a partially dedifferentiated, secretory epithelia characterized by polarization defects and high rates of proliferation and apoptosis (Dell, K., et al., Polycystic kidney disease, in Pediatric Nephrology, E. D. Avner, W. E. Harmon, and P. Niaudet, Editors. 2004, Lippincott Williams & Wilkins: Philadelphia. p. 675-699; Wilson P. D., N Engl J Med, 2004. 350:151-64; Wilson P. D., Int J Biochem Cell Biol, 2004, 36:1868-73; Murcia N. S. et al., Kidney Int, 1999, 55:1187-1197; Harris P. C. and S. Rossetti, Mol Genet Metab, 2004, 81:75-85). It is clear that the development and progressive enlargement of cysts require proliferation of the tubular epithelial cells, transepithelial fluid secretion, and extracellular matrix remodeling (Welling, L. W. and J. J. Grantham, Cystic and developmental diseases of the kidney, in The Kidney, B. M. R. Brenner, F. C., Editor. 1991, WB Saunders: Philadelphia. p. 1657-1694; and Grantham J. J., AM J Kidney Dis, 1996, 28:788-803). Indeed, since the first anatomical studies performed in the 19th century, proliferation has been recognized as the hallmark of cystic epithelia. Cultured epithelial cells from patients or animal models of PKD have consistently demonstrated an increased intrinsic capacity for proliferation and survival (Gabow P. A., N Engl J Med, 1993, 329:332-42; Wilson P. D., N Engl J Med, 2004, 350:151-64; Grantham J. J., AM J Kidney Dis, 1996, 28:788-803; Grantham J. J. et al., Kidney Int, 1987, 31:1145-1152). Therefore, it is expected that an agent effective for treating one type of PKD by inhibiting the proliferation of cystic epithelial cells would also be effective for treating other types of PKD (Avner E. D. and W. E. Sweeney, Pediatr Clin North Am, 2006, 5:889-909; and Torres V. E. and P. C. Harris, J Inter Med, 2007, 261:17-31).

20-HETE Synthesis Inhibitors

The activity and synthesis of 20-HETE are well conserved across animal species. One suitable way to inhibit 20-HETE activity in a human or non-human animal (e.g., a mammal) is to administer a 20-HETE synthesis inhibitor to the human or non-human animal. By "20-HETE synthesis inhibitor," which is used interchangeably with "20-HETE synthesizing enzyme inhibitor," we mean an inhibitor of an enzyme that is involved in converting arachidonic acid to 20-HETE. Such enzymes are known and include those of the CYP4A and CYP4F families such as CYP4A11, CYP4F2, and CYP4F3 (Christmas P et al., *J. Biol. Chem.*, 276: 38166-38172, 2001).

Many classes of 20-HETE synthesis inhibitors are known in the art and they can all be used in the method of the present invention. These inhibitors include those disclosed in WO0132164 (corresponds to U.S. Pat. No. 7,078,400, U.S. Pat. No. 6,864,254, and U.S. patent application publication 20040110830); WO02088071 (corresponds to U.S. Pat. No. 7,214,714); Nakamura T et al., *Bioorg Med Chem.* 12:6209-6219, 2004; Nakamura T et al., *Bioorg Med Chem Lett.* 14:333-336, 2004; Nakamura T et al., *J Med Chem.* 46:5416-5427, 2003; Nakamura T et al., *Bioorg Med Chem Lett.* 14:5305-5308, 2004; Sato M et al., *Bioorg Med Chem Lett.* 11:2993-2995, 2001; Miyata N et al., *Br J Pharmacol.* 133:325-329, 2001; and Xu F et al., *Am J Physiol Regul Integr Comp Physiol* 28:R710-720, 2002, all of which are herein incorporated by reference in their entirety.

Examples of these inhibitors include N-hydroxy-N'-(4-n-butyl-2-methylphenyl)-formamidine (HET0016), N-(3-Chloro-4-morpholin-4-yl)phenyl-N'-hydroxyimidoformamide (TS-011), dibromododecenyl methylsulfonimide (DDMS), 12,12-dibromododec-11-enoic acid (DBDD), 1-aminobenzotriazole (ABT), 17-Octadecynoic acid (17-ODYA), miconazole, ketoconazole, fluconazole, and 10 undecynyl sulfate (10-SUYS). HET0016, TS-011, and DDMS are more specific inhibitors of the synthesis of 20-HETE while 17-ODYA, 1-ABT, and miconazole are less specific inhibitors (WO0236108). HET0016, 1-ABT, and 17-ODYA have been shown to be able to reduce 20-HETE levels in vivo (WO0236108; Dos Santos E A et al., *Am J Physiol Regul Integr Comp Physiol.* 287:R58-68, 2004; Hoagland K M et al., *Hypertension* 42:669-673, 2003; Cambj-Sapunar L et al., *Stroke* 34:1269-1275, 2003; and Hoagland K M et al., *Hypertension* 41:697-702, 2003). A method for synthesizing HET0016 is disclosed in WO0132164. The synthesis of a large number of analogs of HET0016 with similar properties to inhibit the synthesis of 20-HETE have also been described (Nakamura T et al., *Bioorg Med Chem.* 12:6209-6219, 2004; Nakamura T et al., *Bioorg Med Chem Lett.* 14:5305-5308, 2004; Nakamura T et al., *Bioorg Med Chem Lett.* 14:333-336, 2004; Nakamura T et al., *J Med Chem.* 46:5416-5427, 2003; and Sato M et al., *Bioorg Med Chem Lett.* 11:2993-2995, 2001). 17-ODYA, ABT, and miconazole are available from Sigma Chemical Corp., St. Louis, Mo. HET0016 can be purchased from Bio-Mol. Preferred inhibitors for the purpose of the present invention include HET0016, TS-011, and DDMS.

(1) Class I and Class II Hydroxyformamidine Compounds.

The hydroxyformamidine compounds described in WO0132164 (corresponds to U.S. Pat. No. 7,078,400 and U.S. Pat. No. 6,864,254) as 20-HETE synthesis inhibitors can be used in the present invention. For the purpose of the present invention, the hydroxyformamidine compounds represented by the following formula (I) are defined as class I hydroxyformamidine compounds:

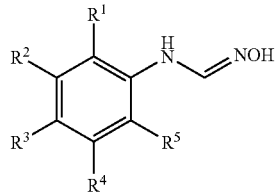

(I)

wherein $R^1$ to $R^5$ are identical or different and represent a hydrogen atom; a hydroxyl group; a carboxyl group; a halogen atom; a $C_{1-14}$ alkyl group; a $C_{1-14}$ alkyl group substituted with 1 to 6 halogen atoms; a $C_{2-6}$ alkenyl group; a $C_{1-6}$ alkoxy $C_{1-6}$ alkyl group; a $C_{3-8}$ cycloalkyl $C_{1-6}$ alkyl group; a $C_{2-6}$ alkynyl group; a $C_{3-8}$ cycloalkyl group; a $C_{3-8}$ cycloalkoxy group; a $C_{2-10}$ alkanoyl group; a $C_{1-6}$ hydroxyalkyl group; a $C_{1-6}$ hydroxyalkyl group substituted with 1 to 6 halogen atoms; a $C_{2-6}$ alkoxycarbonyl group; a 3-phenyl-2-propenyloxycarbonyl group; a $C_{2-6}$ alkoxycarbonyl $C_{1-6}$ alkyl group; a di($C_{1-6}$ alkyl)amino $C_{2-6}$ alkoxycarbonyl group; a mono- or di($C_{1-6}$ alkyl)amino group; a $C_{2-10}$ alkanoylamino group; a $C_{2-6}$ alkanoylamino group substituted with a $C_{1-6}$ alkyl group; a benzoylamino group; a carbamoyl group; a carbamoyl group mono-substituted or di-substituted with $C_{1-6}$ alkyl or phenyl groups; an N—(N',N'-di($C_{1-6}$ alkyl)amino $C_{1-6}$ alkyl) carbamoyl group; a cyano group; a cyano $C_{1-6}$ alkyl group; a nitro group; a thiol group; a phenoxy group; a phenoxy group substituted with 1 to 3 substituents selected from $C_{1-6}$ alkyl groups, $C_{1-6}$ alkoxy groups, and halogen atoms; a phenylthio group; a nitrophenylthio group; a $C_{1-6}$ alkylsulfonyl group; a phenylsulfonyl group; a $C_{1-6}$ alkylthio $C_{1-6}$ alkyl group; a phenylsulfonyl $C_{1-6}$ alkylthio group wherein the benzene ring is substituted with 1 to 5 halogen atoms; a phenyl group; a benzyl group; a phenyl group substituted with 1 to 3 substituents selected from cyano groups, halogen atoms, $C_{1-6}$ alkyl groups, and $C_{1-6}$ alkoxy groups; a biphenyl group; an .alpha.-cyanobenzyl group; an alpha-cyanobenzyl group substituted with 1 to 5 halogen atoms; a benzyl group substituted with a bicyclo[2.2.1]-hept-5-en-2,3-dicarboxylmidyl group; a benzoyl group; a styryl group; a styryl group substituted with 1 to 5 substituents selected from $C_{1-6}$ alkoxy groups and di($C_{1-6}$ alkyl)amino alkyl groups; a pyrrolidino group; a piperidino group; a morpholino group; a pyridyl group; a pyrimidinyl group; a pyrimidinyl group substituted with 1 to 3 substituents selected from $C_{1-6}$ alkyl groups and $C_{1-6}$ alkoxy groups; a phthalimidoyl group; a phthalimidoyl group substituted with 1 to 3 halogen atoms; an N-carbazolyl group; a dioxopiperidinyl group substituted with 1 to 3 $C_{1-6}$ alkyl groups; a phenylsulfonylamino group; a phenylsulfonylamino group substituted with 1 to 3 $C_{1-6}$ alkyl groups; a $C_{1-6}$ alkylaminosulfonyl $C_{1-6}$ alkyl group; a thiadiazolyl group; an oxadiazolyl group; an oxadiazolyl group substituted with a substituted phenyl group wherein the substituents in the substituted phenyl group are 1 to 3 substituents selected from halogen atoms, $C_{1-6}$ alkyl groups, and $C_{1-6}$ alkoxy groups; a pyrrolidinyl group; a pyrazolyl group; a pyrazolyl group substituted with 1 to 3 substituents selected from halogen atoms, $C_{1-6}$ alkyl groups, and trifluoromethyl groups; a furyl group; a furyl group substituted with 1 to 3 substituents selected from halogen atoms, $C_{1-6}$ alkyl groups, and $C_{2-6}$ alkoxycarbonyl groups; a thienopyrimidinylthio group; a thienopyrimidinylthio group substituted with 1 to 3 $C_{1-6}$ alkyl groups; a thienopyridylthio group; a thienopyridylthio group substituted with 1 to 3 $C_{1-6}$ alkyl groups; a benzothiazolylthio group; a benzothiazolylthio group substituted with 1 to 3 halogen atoms; a group represented by the formula: —Y—$(CR^{61}R^{62})_m$—$(CR^{63}R^{64})_n$—$R^7$ [wherein Y represents an oxygen or sulfur atom; $R^6$, $R^{62}$, $R^{63}$, and $R^{64}$ are identical or different and represent a hydrogen atom, a halogen atom, a $C_{1-4}$ alkyl group, or a trifluoromethyl group; $R^7$ represents a hydrogen atom; a halogen atom; a $C_{1-14}$ alkyl group; a $C_{3-8}$ cycloalkyl group; a $C_{3-8}$ cycloalkoxy group; a $C_{2-10}$ alkenyl group; a $C_{2-6}$ alkynyl group; a phenyl group; a phenyl group substituted with 1 to 3 substituents selected from nitro groups, cyano groups, $C_{1-6}$ alkyl groups, $C_{1-6}$ alkoxy groups, $C_{1-6}$ alkylthio groups, phenyl groups, phenoxy groups, phenethyl groups, $C_{2-6}$ alkoxycarbonyl groups, and halogen atoms; a cyano group; a carboxyl group; a $C_{1-6}$ alkoxy group; a $C_{1-6}$ hydroxyalkyl group; a $C_{1-6}$ alkoxy $C_{1-6}$ alkoxy group; a $C_{1-6}$ alkoxy $C_{1-6}$ alkoxy $C_{1-6}$ alkoxy group; a $C_{1-6}$ alkylthio group; a $C_{2-6}$ alkanoyloxy group; a $C_{2-6}$ alkanoyloxy $C_{1-6}$ alkyl group; a phenoxy group; a phenylthio group; an N—($C_{1-6}$ alkyl)toluidino group; a pyrrolidino group; a piperidino group; a morpholino group; a pyridyl group; a pyridyl group substituted with a $C_{1-6}$ alkyl group; a piperidino group substituted with a $C_{1-6}$ alkyl group; a pyridyl group substituted with a $C_{1-6}$ alkoxy group; a pyrrolidino group substituted with a $C_{1-6}$ alkyl group; a morpholino group substituted with a $C_{1-6}$ alkyl group; a morpholinyl group; a morpholinyl group substituted with a $C_{1-6}$ alkyl group; a homomorpholinyl group; a thiomorpholino group; a thiomorpholino group substituted with a $C_{1-6}$ alkyl group; a thiomorpholinyl group; a thiomorpholinyl group substituted with a $C_{1-6}$ alkyl group; a piperadinyl group; a piperadin-1-yl group substituted with a $C_{1-6}$ alkyl group at the 4-position; a homopiperidinyl group; a homopiperidinyl group substituted with a $C_{1-6}$ alkyl group; a pyridylthio group; a quinolyl group; a furyl group; an oxetanyl group; an oxolanyl group; a dioxolanyl group; a dioxolanyl group substituted with a $C_{1-6}$ alkyl group; an oxanyl group; a dioxanyl group; a dioxanyl group substituted with a $C_{1-6}$ alkyl group; a benzodioxanyl group; a pyrrolidon-1-yl group; a pyrrolidinyl group; an N—($C_{1-6}$ alkyl)pyrrolidinyl group; a piperidinyl group; an N—($C_{1-6}$ alkyl)piperidinyl group; a pyrrolyl group; a thienyl group; a thiazolyl group; a thiazolyl group substituted with 1 to 3 $C_{1-6}$ alkyl groups; a 2,6-purindion-7-yl group substituted with $C_{1-6}$ alkyl group(s); a furfuryl group; a di($C_{1-6}$ alkyl)amino group; a $C_{2-6}$ alkoxycarbonyl group; or a di($C_{1-6}$ alkyl)amino $C_{1-6}$ alkoxy group; m is an integer of 1 to 6; and n is an integer of 0 to 6]; or a group represented by the formula: —$SO_2NR^8R^9$ [wherein $R^8$ and $R^9$ are identical or different and represent a hydrogen atom, a $C_{1-10}$ alkyl group, a $C_{2-6}$ alkanoyl group, an isoxazolyl group, an isoxazolyl group substituted with 1 to 3 $C_{1-6}$ alkyl groups, a thiadiazolyl group, a thiadiazolyl group substituted with 1 to 3 $C_{1-6}$ alkyl groups, a thiazolyl group, a thiazolyl group substituted with 1 to 3 $C_{1-6}$ alkyl groups, a pyridyl group, a pyridyl group substituted with 1 to 3 $C_{1-6}$ alkyl groups, a pyrimidinyl group, a pyrimidinyl group substituted with 1 to 3 $C_{1-6}$ alkyl groups, a pyrimidinyl group substituted with 1 to 3 $C_{1-6}$ alkoxy groups, a pyridazinyl group, a pyridazinyl group substituted with 1 to 3 $C_{1-6}$ alkoxy groups, an indazolyl group, or a carbamoyl group mono- or di-substituted with $C_{1-6}$ alkyl groups, or alternatively, taken together with the nitrogen atom to which they are bonded, form a 3,5-dioxopiperadino group, a pyrrolidinyl group, a piperidino group, or a morpholino group], or alternatively, the two groups adjacent to each other of $R^1$ to $R^5$, taken together with the benzene ring to which they are bonded, form a phthalimide ring; a phthalimide ring substituted with a $C_{1-6}$ alkyl group; an indole ring; an indane ring; an indazole ring; a benzotriazole ring; an S,S-dioxobenzothiophene ring; a 2,3-dihydroimidazo[2,1-b]benzothiazole ring; a dibenzofuran ring; a dibenzofuran ring substituted with a $C_{1-6}$ alkoxy group; a fluorene ring; a fluorene ring substituted with a halogen atom; a pyrene ring; a carbostyryl ring; a carbostyryl ring substituted with a $C_{1-6}$ alkyl group; a naphthalene ring; a naphthalene ring substituted with 1 to 3 substituents selected from cyano groups, halogen atoms, nitro groups, and $C_{1-6}$ alkyl groups; a 1,2,3,4-tetrahydronaphthalene ring; a quinoline ring; a quinoline ring substituted with a $C_{1-6}$ alkyl group; an isoquinoline ring; a 2-oxo-alpha-chromene ring; a 2-oxo-alpha-chromene ring substituted with 1 to 3 substituents selected from $C_{1-6}$ alkyl groups, $C_{1-6}$ alkoxy groups, and $C_{1-6}$ alkoxy $C_{1-6}$ alkyl groups; a cinnolin ring; a cinnolin ring substituted with a $C_{1-6}$ alkyl group; a phthalazindione ring; a benzothiazol ring; a benzothiazol ring substituted with a $C_{1-6}$ alkyl group; a benzodioxorane ring; or a benzobutyrolactone ring, or a pharmaceutically-acceptable salt of a hydroxyformamidine compound represented by formula (I) above.

For the purpose of the present invention, the hydroxyformamidine compounds represented by the following formula (II) are defined as class II hydroxyformamidine compounds:

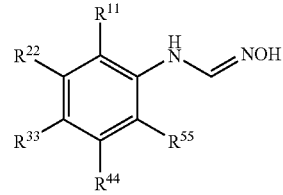

(II)

wherein at least one of $R^{11}$ to $R^{55}$ represents a $C_{5-14}$ alkyl group; a $C_{1-14}$ alkyl group substituted with 1 to 6 halogen atoms; a $C_{2-6}$ alkenyl group; a $C_{3-8}$ cycloalkyl $C_{1-6}$ alkyl group; a $C_{3-8}$ cycloalkyl group; a $C_{3-8}$ cycloalkoxy group; a $C_{2-10}$ alkanoyl group; a $C_{1-6}$ hydroxyalkyl group; a $C_{1-6}$ hydroxyalkyl group substituted with 1 to 6 halogen atoms; a $C_{2-6}$ alkoxycarbonyl group; a 3-phenyl-2-propenyloxycarbonyl group; a $C_{2-6}$ alkoxycarbonyl $C_{1-6}$ alkyl group; a di($C_{1-6}$ alkyl)amino $C_{2-6}$ alkoxycarbonyl group; a mono- or di($C_{1-6}$ alkyl)amino group; a $C_{2-10}$ alkanoylamino group; a $C_{2-6}$ alkanoylamino group substituted with a $C_{1-6}$ alkyl group; a benzoylamino group; a carbamoyl group; a carbamoyl group mono-substituted or di-substituted with $C_{1-6}$ alkyl or phenyl groups; an N—(N',N'-di($C_{1-6}$ alkyl)amino $C_{1-6}$ alkyl)carbamoyl group; a cyano group; a cyano $C_{1-6}$ alkyl group; a $C_{1-6}$ alkylsulfonyl group; a phenylsulfonyl group; a $C_{1-6}$ alkylthio $C_{1-6}$ alkyl group; a phenylsulfonyl $C_{1-6}$ alkylthio group wherein the benzene ring is substituted with 1 to 5 halogen atoms; a phenyl group; a benzyl group; a phenyl group substituted with 1 to 3 substituents selected from cyano groups, halogen atoms, $C_{1-6}$ alkyl groups, and $C_{1-6}$ alkoxy groups; a biphenyl group; an .alpha.-cyanobenzyl group; an alpha-cyanobenzyl group substituted with 1 to 5 halogen atoms; a benzyl group substituted with a bicyclo[2.2.1]-hept-5-en-2,3-dicarboxylmidyl group; a benzoyl group; a styryl group; a styryl group substituted with 1 to 5 substituents selected from $C_{1-6}$ alkoxy groups and di($C_{1-6}$ alkyl)amino alkyl groups; a pyrrolidin-1-yl group; a piperidino group; a morpholino group; a pyridyl group; a pyrimidinyl group; a pyrimidinyl group substituted with 1 to 3 substituents selected from $C_{1-6}$ alkyl groups and $C_{1-6}$ alkoxy groups; a phthalimidoyl group; a phthalimidoyl group substituted with 1 to 3 halogen atoms; an N-carbazolyl group; a dioxopiperidinyl group substituted with 1 to 3 $C_{1-6}$ alkyl groups; a phenylsulfonylamino group; a phenylsulfonylamino group substituted with 1 to 3 $C_{1-6}$ alkyl groups; a $C_{1-6}$ alkylaminosulfonyl $C_{1-6}$ alkyl group; a thiadiazolyl group; an oxadiazolyl group; an oxadiazolyl group substituted with a substituted phenyl group wherein the substituents in the substituted phenyl group are 1 to 3 substituents selected from halogen atoms, $C_{1-6}$ alkyl groups, and $C_{1-6}$ alkoxy groups; a pyrrolidinyl group; a pyrazolyl group; a pyrazolyl group substituted with 1 to 3 substituents selected from halogen atoms, $C_{1-6}$ alkyl groups, and trifluoromethyl groups; a furyl group; a furyl group substituted with 1 to 3 substituents selected from halogen atoms, $C_{1-6}$ alkyl groups, and C$_{2-6}$ alkoxycarbonyl groups; a thienopyrimidinylthio group; a thienopyrimidinylthio group substituted with 1 to 3 C$_{1-6}$ alkyl groups; a thienopyridylthio group; a thienopyridylthio group substituted with 1 to 3 C$_{1-6}$ alkyl groups; a benzothiazolylthio group; a benzothiazolylthio group substituted with 1 to 3 halogen atoms; a group represented by the formula: —Y—(CR$^{61}$R$^{62}$)$_m$—(CR$^{63}$R$^{64}$)$_n$—R$^{77}$ [wherein Y represents an oxygen or sulfur atom; R$^{61}$, R$^{62}$, R$^{63}$, and R$^{64}$ are identical or different and represent a hydrogen atom, a halogen atom, a C$_{1-4}$ alkyl group, or a trifluoromethyl group; R$^{77}$ represents a halogen atom; a C$_{4-14}$ alkyl group; a C$_{3-8}$ cycloalkyl group; a C$_{2-10}$ alkenyl group; a C$_{2-6}$ alkynyl group; a phenyl group; a phenyl group substituted with 1 to 3 substituents selected from nitro groups, cyano groups, C$_{1-6}$ alkyl groups, C$_{1-6}$ alkoxy groups, C$_{1-6}$ alkylthio groups, phenyl groups, phenoxy groups, phenethyl groups, C$_{2-6}$ alkoxycarbonyl groups, and halogen atoms; a cyano group; a carboxyl group; a C$_{1-6}$ alkoxy group; a C$_{1-6}$ alkoxy C$_{1-6}$ alkoxy group; a C$_{1-6}$ alkoxy C$_{1-6}$ alkoxy C$_{1-6}$ alkoxy group; a C$_{1-6}$ hydroxyalkyl group; a C$_{3-8}$ cycloalkoxy group; a C$_{1-6}$ alkylthio group; a C$_{2-6}$ alkanoyloxy group; a C$_{2-6}$ alkanoyloxy C$_{1-6}$ alkyl group; a phenoxy group; a phenylthio group; an N—(C$_{1-6}$ alkyl)toluidino group; a pyrrolidin-1-yl group; a piperidino group; a morpholino group; a pyridyl group; a pyridyl group substituted with a C$_{1-6}$ alkyl group; a piperidino group substituted with a C$_{1-6}$ alkyl group; a pyridyl group substituted with a C$_{1-6}$ alkoxy group; a pyrrolidin-1-yl group substituted with a C$_{1-6}$ alkyl group; a morpholino group substituted with a C$_{1-6}$ alkyl group; a morpholinyl group; a morpholinyl group substituted with a C$_{1-6}$ alkyl group; a homomorpholinyl group; a thiomorpholino group; a thiomorpholino group substituted with a C$_{1-6}$ alkyl group; a thiomorpholinyl group; a thiomorpholinyl group substituted with a C$_{1-6}$ alkyl group; a piperazinyl group; a piperazin-1-yl group substituted with a C$_{1-6}$ alkyl group at the 4-position; a homopiperidinyl group; a homopiperidinyl group substituted with a C$_{1-6}$ alkyl group; a pyridylthio group; a quinolyl group; a furyl group; an oxetanyl group; an oxolanyl group; a dioxolanyl group; a dioxolanyl group substituted with a C$_{1-6}$ alkyl group; an oxanyl group; a dioxanyl group; a dioxanyl group substituted with a C$_{1-6}$ alkyl group; a benzodioxanyl group; a pyrrolidon-1-yl group; a pyrrolidinyl group; an N—(C$_{1-6}$ alkyl)pyrrolidinyl group; a piperidinyl group; an N—(C$_{1-6}$ alkyl)piperidinyl group; a pyrrolyl group; a thienyl group; a thiazolyl group; a thiazolyl group substituted with 1 to 3 C$_{1-6}$ alkyl groups; a 2,6-purindion-7-yl group substituted with C$_{1-6}$ alkyl group(s); a furfuryl group; a di(C$_{1-6}$ alkyl)amino group; a C$_{2-6}$ alkoxycarbonyl group; or a di(C$_{1-6}$ alkyl)amino C$_{1-6}$ alkoxy group; m is an integer of 1 to 6; and n is an integer of 0 to 6]; or a group represented by the formula: —SO$_2$NR$^8$R$^9$ [wherein R$^8$ and R$^9$ are identical or different and represent a hydrogen atom, a C$_{1-10}$ alkyl group, a C$_{2-6}$ alkanoyl group, an isoxazolyl group, an isoxazolyl group substituted with 1 to 3 C$_{1-6}$ alkyl groups, a thiadiazolyl group, a thiadiazolyl group substituted with 1 to 3 C$_{1-6}$ alkyl groups, a thiazolyl group, a thiazolyl group substituted with 1 to 3 C$_{1-6}$ alkyl groups, a pyridyl group, a pyridyl group substituted with 1 to 3 C$_{1-6}$ alkyl groups, a pyrimidinyl group, a pyrimidinyl group substituted with 1 to 3 C$_{1-6}$ alkyl groups, a pyrimidinyl group substituted with 1 to 3 C$_{1-6}$ alkoxy groups, a pyridazinyl group, a pyridazinyl group substituted with 1 to 3 C$_{1-6}$ alkoxy groups, an indazolyl group, or a carbamoyl group mono- or di-substituted with C$_{1-6}$ alkyl groups, or alternatively, taken together with the nitrogen atom to which they are bonded, form a 3,5-dioxopiperazin-1-yl group, a pyrrolidinyl group, a piperidino group, or a morpholino group], or alternatively, the two groups adjacent to each other of R$^{11}$ to R$^{55}$, taken together with the benzene ring to which they are bonded, form a phthalimide ring; a phthalimide ring substituted with a C$_{1-6}$ alkyl group; an indole ring; an indane ring; an indazole ring; a benzotriazole ring; an S,S-dioxobenzothiophene ring; a 2,3-dihydroimidazo[2,1-b]benzothiazole ring; a dibenzofuran ring; a dibenzofuran ring substituted with a C$_{1-6}$ alkoxy group; a fluorene ring; a fluorene ring substituted with a halogen atom; a pyrene ring; a carbostyryl ring; a carbostyryl ring substituted with a C$_{1-6}$ alkyl group; a naphthalene ring; a naphthalene ring substituted with 1 to 3 substituents selected from cyano groups, halogen atoms, nitro groups, and C$_{1-6}$ alkyl groups; a 1,2,3,4-tetrahydronaphthalene ring; a quinoline ring; a quinoline ring substituted with a C$_{1-6}$ alkyl group; an isoquinoline ring; a 2-oxo-alpha-chromene ring; a 2-oxo-alpha-chromene ring substituted with 1 to 3 substituents selected from C$_{1-6}$ alkyl groups, C$_{1-6}$ alkoxy groups, and C$_{1-6}$ alkoxy C$_{1-6}$ alkyl groups; a cinnolin ring; a cinnolin ring substituted with a C$_{1-6}$ alkyl group; a phthalazindione ring; a benzothiazol ring; a benzothiazol ring substituted with a C$_{1-6}$ alkyl group; a benzodioxorane ring; or a benzobutyrolactone ring, and the remaining groups of R$^{11}$ to R$^{55}$ are identical or different and represent a hydrogen atom, a C$_{1-6}$ alkyl group, a C$_{1-4}$ alkoxy group, a trifluoromethyl group, a nitro group, or a halogen atom, or a pharmaceutically-acceptable salt of a hydroxyformamidine compound represented by formula (II) above.

The terms used in defining the compounds represented by formula (I) or (II) are defined in the following. "C$_{x-y}$" means that the group following the "C$_{x,y}$" has the number of x-y of carbon atoms.

The term "halogen atom" refers to a fluorine, chlorine, bromine, or iodine atom.

The term "C$_{1-4}$, C$_{1-6}$, C$_{1-8}$, and C$_{1-14}$ alkyl group" means straight-chain or branched alkyl groups having 1 to 4, 1 to 6, 1 to 8, and 1 to 14 carbon atoms, respectively.

The term "C$_{1-14}$ alkyl group substituted with 1 to 6 halogen atoms" means a straight-chain or branched alkyl group having 1 to 14 carbon atoms, substituted with 1 to 6 halogen atoms.

The term "C$_{2-6}$ alkenyl" means a straight-chain or branched alkynyl group having a double bond, and 2 to 6 carbon atoms.

The term "C$_{2-6}$ alkynyl group" means a straight-chain or branched alkynyl group having a triple bond, and 2 to 6 carbon atoms.

The term "C$_{3-8}$ cycloalkyl group" means a cyclic alkyl group having 3 to 8 carbon atoms, including, for example, a cyclopropyl group, a cyclopentyl group, or a cyclohexyl group, or the like.

The term "C$_{3-8}$ cycloalkyl C$_{1-6}$ alkyl group" means a group having a combined structure of a C$_{3-8}$ cycloalkyl group and a C$_{1-6}$ alkyl group, including, for example, a cyclopropylmethyl group, a cyclobutylmethyl group, a cyclopentylmethyl group, or a cyclohexylmethyl group, or the like.

The term C$_{1-6}$ alkoxy group" means a straight-chain or branched alkoxy group having 1 to 6 carbon atoms.

The term "C$_{1-6}$ alkoxy C$_{1-6}$ alkyl group" means a group having a combined structure of a C$_{1-6}$ alkoxy group and a C$_{1-6}$ alkyl group.

The term "C$_{3-8}$ cycloalkoxy group" means a cyclic alkoxy group having 3 to 8 carbon atoms, including, for example, a cyclopropyloxy group, a cyclopentyloxy group, or a cyclohexyloxy group, or the like.

The term "C$_{2-10}$ alkanoyl group" means a straight-chain or branched alkanoyl group having 2 to 10 carbon atoms.

The term "$C_{1-6}$ hydroxyalkyl" means a $C_{1-6}$ alkyl group substituted with hydroxyl group(s).

The term "$C_{2-6}$ alkanoyloxy $C_{1-6}$ alkyl group" means a group wherein the hydroxyl group(s) of above $C_{1-6}$ hydroxyalkyl group is/are substituted with $C_{2-6}$ alkanoyloxy group(s).

The term "$C_{1-6}$ hydroxyalkyl group substituted with 1 to 6 halogen atoms" means a $C_{1-6}$ hydroxyalkyl group substituted with 1 to 6 halogen atoms.

The term "$C_{2-6}$ alkoxycarbonyl group" means a group having a combined structure of a straight-chain or branched $C_{1-5}$ alkoxy group and a carbonyl group.

The term "$C_{2-6}$ alkoxycarbonyl $C_{1-6}$ alkyl group" means a group having a combined structure of a $C_{2-6}$ alkoxycarbonyl group and a $C_{1-6}$ alkoxy group. Therefore, a $C_{2-6}$ alkoxycarbonyl $C_{1-6}$ alkyl group may be represented by the general formula: —$(CH_2)_k$—$COOR^{14}$ (wherein k is an integer of 1 to 6; $R^{14}$ is a $C_{1-6}$ alkyl group).

The term "di($C_{1-6}$ alkyl)amino $C_{2-6}$ alkoxycarbonyl" means a group having a combined structure of an amino group substituted with two $C_{1-6}$ alkyl groups and a $C_{2-6}$ alkoxycarbonyl group.

The term "mono- or di($C_{1-6}$ alkyl)amino group" means an amino group substituted with one or two $C_{1-6}$ alkyl groups.

The term "$C_{2-10}$ alkanoylamino group" means an amino group substituted with a $C_{2-10}$ alkanoyl group. In addition, as an example of "$C_{2-10}$ alkanoylamino group substituted with $C_{1-6}$ alkyl", mention may be made of an N-acetyl-N-methylamino group. Examples of "carbamoyl group mono- or di-substituted with $C_{1-6}$ alkyl or phenyl groups" include an N-methylcarbamoyl group, a N-butylcarbamoyl group, or an N-phenylcarbamoyl group. An example of "N—(N',N'-di($C_{1-6}$ alkyl)amino $C_{1-6}$ alkyl)carbamoyl group" is an N—(N',N'-diethylaminoethyl)carbamoyl group.

The term "cyano $C_{1-6}$ alkyl group" means a group having a combined structure of a cyano group and a $C_{1-6}$ alkyl group.

Examples of "phenoxy group substituted with 1 to 3 substituents selected from nitro groups, thiol groups, phenoxy groups, $C_{1-6}$ alkyl groups, $C_{1-6}$ alkoxy groups, and halogen atoms" include a 2-methylphenoxy group, a 3-methylphenoxy group, a 4-methylphenoxy group, a 2-methoxyphenoxy group, a 3-methoxyphenoxy group, a 4-methoxyphenoxy group, a 2-chlorophenoxy group, a 3-chlorophenoxy group, or a 4-chlorophenoxy group, or the like.

The term "$C_{1-6}$ alkylsulfonyl group" means a group having a combined structure of a $C_{1-6}$ alkyl group and a sulfonyl group (—$SO_2$—).

The term "$C_{1-6}$ alkylthio $C_{1-6}$ alkyl group" means a group having a combined structure of a $C_{1-6}$ alkylthio group and a $C_{1-6}$ alkyl group.

The term "phenylsulfonyl $C_{1-6}$ alkylthio wherein the benzene ring is substituted with 1 to 5 halogen atoms" means a group having a combined structure of a substituted phenylsulfonyl group and a $C_{1-6}$ alkylthio group.

Examples of the "phenyl group substituted with 1 to 3 substituents selected from cyano groups, halogen atoms, $C_{1-6}$ alkyl groups, and $C_{1-6}$ alkoxy groups" include a 4-cyanophenyl group, a 4-chlorophenyl group, a 4-methylphenyl group, or a 4-methoxyphenyl group, or the like. As the "alpha-cyanobenzyl group substituted with 1 to 5 halogen atoms", for example, an alpha-cyano-4-chlorobenzyl group or the like.

Examples of the "styryl group substituted with 1 to 5 substituents selected from $C_{1-6}$ alkoxy groups and di($C_{1-6}$ alkyl) amino alkyl groups" include a 4-methoxystyryl group, or an 4-N,N-dimethylaminostyryl group, or the like.

Examples of the "pyrimidinyl group substituted with 1 to 3 substituents selected from $C_{1-6}$ alkyl groups and $C_{1-6}$ alkoxy groups" include a 6-methoxypyrimidin-4-yl group, or a 2-methylpyrimidin-4-yl group, or the like.

An example of the "phthalimidoyl group substituted with 1 to 3 halogen atoms" is a 5-chloro-N-phthalimidoyl group or the like.

An example of the "dioxopiperidinyl group substituted with 1 to 3 $C_{1-6}$ alkyl groups" is a 2,6-dioxo-3-ethylpiperidin-3-yl group or the like.

An example of the "phenylsulfonylamino group substituted with 1 to 3 $C_{1-6}$ alkyl groups" is a 4-methylphenylsulfonylamino group or the like. An example of the "$C_{1-6}$ alkylaminosulfonyl $C_{1-6}$ alkyl group" is a methylaminosulfonylmethyl group or the like.

An example of the "oxadiazolyl group substituted with substituted phenyl group wherein the substituents in the substituted phenyl group are 1 to 3 substituents selected from halogen atoms, $C_{1-6}$ alkyl groups, and $C_{1-6}$ alkoxy groups" is a group wherein an oxadiazole ring is substituted with a phenyl group substituted with a tert-butyl group, or a methoxy group, or a bromine atom.

An example of "pyrazolyl group substituted with 1 to 3 substituents selected from halogen atoms, $C_{1-6}$ alkyl groups, and trifluoromethyl groups" is a 3-trifluoromethylpyrazolyl group or the like.

An example of "furyl group substituted with 1 to 3 substituents selected from halogen atoms, $C_{1-6}$ alkyl groups, and $C_{2-6}$ alkoxycarbonyl groups" is a furyl group substituted with a methyl group, or an ethoxycarbonyl group, or the like.

As the "thienopyrimidinylthio group substituted with 1 to 3 $C_{1-6}$ alkyl groups", a substituted thienopyrimidinylthio group wherein the fused ring is substituted with one methyl or ethyl group is preferable, and more particularly, a group wherein a thiophene ring is substituted with a methyl group is more preferable.

As the "thienopyridylthio group substituted with 1 to 3 $C_{1-6}$ alkyl groups", a substituted thienopyridylthio group wherein the fused ring is substituted with one methyl or ethyl group is preferable, and more particularly, a group wherein a thiophene ring is substituted with a methyl group is more preferable.

As the "benzothiazolylthio group substituted with 1 to 3 halogen atoms", a benzothiazolylthio group wherein the fused ring is substituted with one halogen atom is preferable.

As the "isoxazolyl group substituted with 1 to 3 $C_{1-6}$ alkyl groups", an isoxazolyl group substituted with one or two methyl or ethyl groups is preferable.

As the "thiazolyl group substituted with 1 to 3 $C_{1-6}$ alkyl groups", a thiazolyl group substituted with one or two methyl or ethyl groups is preferable.

As the "pyridyl group substituted with 1 to 3 $C_{1-6}$ alkyl groups", a pyridyl group substituted with one or two methyl or ethyl groups, and in particular, a 2-methylpyridin-6-yl group is preferable.

As the "pyrimidinyl group substituted with 1 to 3 $C_{1-6}$ alkyl groups", a pyrimidinyl group substituted with one or two methyl or ethyl groups is preferable, and more particularly, a 2,4-dimethylpyrimidin-6-yl group is more preferable.

As the "pyrimidinyl group substituted with 1 to 3 $C_{1-6}$ alkoxy groups", a pyrimidinyl group substituted with one or two methoxy or ethoxy groups is preferable, and more particularly, a 4-methoxypyrimidin-6-yl group, or a 2,4-dimethylpyrimidin-6-yl group is more preferable.

As the "pyridazinyl group substituted with 1 to 3 $C_{1-6}$ alkoxy groups", a pyridazinyl group substituted with one or two methoxy or ethoxy groups is preferable.

The term "$C_{2-10}$ alkenyl group" means a straight-chain or branched alkenyl group having a double bond, and 2 to 10 carbon atoms.

The term "$C_1$-6 alkylthio group" means a straight-chain or branched alkylthio group having 1 to 6 carbon atoms.

The term "$C_{2-6}$ alkanoyloxy group" means a group having a combined structure of a $C_{2-6}$ alkanoyl group and an oxy group (—O—).

Examples of "phenyl group substituted with 1 to 3 substituents selected from nitro groups, cyano groups, $C_{1-6}$ alkyl groups, $C_{1-6}$ alkoxy groups, $C_{1-6}$ alkylthio groups, phenyl groups, phenoxy groups, phenethyl groups, $C_{2-6}$ alkoxycarbonyl groups, and halogen atoms" include a 4-chlorophenyl group, a 4-fluorophenyl group, a 2,5-difluorophenyl group, a 2,5-dichlorophenyl group, an o-phenethylphenyl group, a 4-methylthiophenyl group, a m-phenoxyphenyl group, a 4-methylphenyl group, a 3-methylphenyl group, a 2-methylphenyl group, a 2-methoxyphenyl group, a 3-methoxyphenyl group, a 4-methoxyphenyl group, a 2,3-dimethoxyphenyl group, a 2,4-dimethoxyphenyl group, a 4-methoxycarbonylphenyl group, a p-phenylphenyl group, or a m-cyanophenyl group, or the like.

The term "$C_1$-6 alkoxy $C_{1-6}$ alkoxy group" means a group having a combined structure of a $C_{1-6}$ alkoxy group and a $C_{1-6}$ alkoxy group.

Examples of the "$C_{1-6}$ alkoxy $C_{1-6}$ alkoxy $C_{1-6}$ alkoxy group" include $CH_3OCH_2CH_2OCH_2CH_2O$— and the like.

Examples of the "di($C_{1-6}$ alkyl)amino group" include —$N(CH_3)_2$, —$N(CH_2CH_3)_2$, —$N(CH_2CH_2CH_3)_2$, and the like.

Examples of the "di($C_{1-6}$ alkyl)amino $C_{1-6}$ alkoxy group" include $OCH_2N(CH_3)_2$, —$OCH_2CH_2N(CH_3)_2$—, —$OCH_2CH_2N(CH_2CH_3)_2$, and the like.

The term "N—($C_{1-6}$ alkyl)toluidino group" means a group having a structure wherein a toluidino group ($CH_3$—$C_6H_4$—NH—) is substituted with a $C_{1-6}$ alkyl group.

The "furyl group" includes a 2-furyl or 3-furyl group.

The "oxetanyl group" has a structure of a saturated 4-membered ring having one oxygen atom as a hetero atom, and includes a 2-oxetanyl group, or a 3-oxetanyl group.

The "oxolanyl group" has a structure of a saturated 5-membered ring having one oxygen atom as a hetero atom, and includes a 2-oxolanyl group, or a 3-oxolanyl group. The "dioxolanyl group" refers to a mono-valent group derived by eliminating hydrogen atom from a saturated 5-membered ring having two oxygen atoms as hetero atoms (dioxolane).

The "oxanyl group" has a structure of a saturated 6-membered ring having one oxygen atom as a hetero atom, and includes a 2-oxanyl, a 3-oxanyl group, or a 4-oxanyl group.

The "dioxanyl group" refers to a mono-valent group derived by eliminating hydrogen atom from a saturated 6-membered ring having two oxygen atoms as hetero atoms (dioxane The "benzodioxanyl group" refers to a mono-valent group derived by eliminating hydrogen atom from a benzodioxane ring.

The "piperidinyl group" includes a 2-piperidinyl, a 3-piperidinyl group, or a 4-piperidinyl group. In addition, in the piperidinyl group, the nitrogen atom present therein may be substituted with a $C_{1-6}$ alkyl group.

The "piperidino group" refers to a mono-valent group derived by eliminating a hydrogen atom present on the nitrogen atom of piperidine.

The "pyridyl group" includes a 2-pyridyl group, a 3-pyridyl group, or a 4-pyridyl group. In the pyridyl group, the ring thereof maybe substituted with a $C_{1-6}$ alkyl group.

The "pyridylthio group" has a combined structure of a pyridyl group and one thio group, and includes a pyridin-2-ylthio group, a pyridin-3-ylthio group, or a pyridin-4-ylthio group.

The "pyrrolidino group" refers to a mono-valent group derived by eliminating a hydrogen atom present on the nitrogen atom of pyrrolidine.

The "pyrrolidon-1-yl group" includes a 2-pyrrolidon-1-yl or 3-pyrrolidon-1-yl group.

The "pyrrolidinyl group" includes a 2-pyrrolidinyl group or 3-pyrrolidinyl group. In the pyrrolidinyl group, the nitrogen atom present thereon may be substituted with a $C_{1-6}$ alkyl group.

The "quinolyl" includes a 2-quinolyl group, a 3-quinolyl group, a 4-quinolyl group, a 5-quinolyl group, a 6-quinolyl group, a 7-quinolyl group, or a 8-quinolyl group. The "pyrrolyl group" includes a 1-pyrrolyl group, a 2-pyrrolyl group, or a 3-pyrrolyl group.

The "thienyl group" includes a 2-thienyl group, or a 3-thienyl group.

The "thiazolyl group" includes a 2-thiazolyl group, a 4-thiazolyl group, or a 5-thiazolyl group. In addition, in the thiazolyl group, the ring thereof may be substituted with a $C_{1-6}$ alkyl group.

The "morpholino group" refers to a mono-valent group derived by eliminating a hydrogen atom present on the nitrogen atom of morpholine.

The "furfuryl group" means a 2-furfuryl group.

The "2,6-purindion-7-yl group" refers to a mono-valent group derived from 2,6-purindione wherein oxo groups (=O) are bonded to the carbon atoms at the 2-position and the 6-position of the purine ring and a group derived by eliminating the hydrogen atom present on the nitrogen atom at the 7-position. For the "2,6-purindion-7-yl substituted with $C_{1-6}$ alkyl group(s)", it is preferable that one or two nitrogen atoms on the group be substituted with a $C_{1-6}$ alkyl group.

Any two groups of $R^1$ to $R^5$ adjacent to each other in formula (I) or (II), taken together with the benzene ring to which they are bonded, may form the ring structures described above. In these rings, the following rings may be specially mentioned.

As the "phthalimide ring substituted with a $C_{1-6}$ alkyl group", a ring substituted with a methyl or ethyl group is preferable.

As the "dibenzofuran ring substituted with a $C_{1-6}$ alkoxy group", a ring substituted with a methoxy or ethoxy group is preferable.

As the "fluorene ring substituted with a halogen atom", a ring substituted with a chlorine or bromine atom is preferred.

As the "carbostyryl ring substituted with a $C_{1-6}$ alkyl group", a ring substituted with a methyl or ethyl group is preferable.

As the "naphthalene ring substituted with 1 to 3 substituents selected from cyano groups, halogen atoms, nitro groups, and $C_{1-6}$ alkyl groups", a ring substituted with 1 to 3 cyano groups, halogen atoms, nitro groups, methyl groups or ethyl groups is preferable.

As the "quinoline ring substituted with a $C_{1-6}$ alkyl group", a ring substituted with a methyl or ethyl group is preferred.

As the "2-oxo-alpha-chromene ring substituted with 1 to 3 substituents selected from $C_{1-6}$ alkyl groups, $C_{1-6}$ alkoxy groups, and $C_{1-6}$ alkoxy $C_{1-6}$ alkyl groups", a ring substituted with a methyl group, an ethyl group, a methoxy group, an ethoxy group, a methoxymethyl group, a methoxyethyl group, an ethoxymethyl group, or an ethoxyethyl group is preferred.

As the "cinnolin ring substituted with a $C_{1-6}$ alkyl group", a ring substituted with a methyl or ethyl group is preferred.

As the "benzothiazol ring substituted with a $C_{1-6}$ alkyl group", the ring substituted with a methyl or ethyl group is preferred.

The pharmaceutically acceptable salt is a salt with alkaline metal, alkaline earth metal, ammonium, alkylammonium, etc. and a salt with mineral acid or organic acid. Its examples are sodium salt, potassium salt, calcium salt, ammonium salt, aluminum salt, triethylammonium salt, acetate, propionate, butyrate, formate, trifluoroacetate, maleate, tartrate, citrate, stearate, succinate, ethylsuccinate, lactobionate, gluconate, glucoheptonate, benzoate, methanesulfonate, ethanesulfonate, 2-hydroxyethanesulfonate, benzenesulfonate, p-toluenesulfonate, laurylsulfate, malate, aspartate, glutamate, adipate, a salt with cysteine, a salt with N-acetylcysteine, hydrochloride, hydrobromide, phosphate, sulfate, hydroiodide, nicotinate, oxalate, picrate, thiocyanate, undecanoate, a salt with acrylic acid polymer and a salt with carboxyvinyl polymer.

(2) Class III Hydroxyformamidine Compounds.

The hydroxyformamidine compounds described in WO02088071 (corresponds to U.S. Pat. No. 7,214,714) as 20-HETE synthesis inhibitors can be used in the present invention. For the purpose of the present invention, these inhibitors are defined as class III hydroxyformamidine compounds, which are represented by the following formula (III) or pharmaceutically acceptable salts thereof:

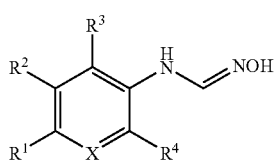

(III)

wherein $R_1$ represents a substituted morpholino group, a substituted piperidino group, a piperazin-1-yl group, a substituted piperazin-1-yl group, a thiomorpholin-1-yl group, a perhydroazepin-1-yl group, a perhydroazocin-1-yl group, a tetrahydropyridin-1-yl group, a pyrrolin-1-yl group, a 1,4-dioxa-8-azaspiro[4,5]decan-8-yl group, a decahydroquinolin-1-yl group, a mono or di($C_{1-4}$ alkoxy $C_{1-6}$ alkyl)amino group, or a mono or di($C_{1-4}$ hydroxyalkyl)amino group; X represents a nitrogen atom or a group represented by $CR^5$; and $R^2$ to $R^5$ are the same or different and each represents a hydrogen atom, a $C_{1-4}$ alkyl group, a $C_{1-4}$ alkoxy group, a trifluoromethyl group or a halogen atom.

The terms used in defining the compounds represented by formula (III) are defined in the following. The substituted morpholino group means a morpholino group which is substituted with 1 to 3 $C_{1-4}$ alkyl group(s) and its examples are 2-methylmorpholino group, 2-ethylmorpholino group, 3-methylmorpholino group, 2,6-dimethylmorpholino group and 2,3,5-trimethylmorpholino group where 2,6-dimethylmorpholino group is more preferred.

The substituted piperidino group means a piperidino group which is substituted with a $C_{1-4}$ alkyl group, a piperidino group which is substituted with a $C_{1-4}$ alkoxy group, a piperidino group which is substituted with a hydroxyl group, a piperidino group which is substituted with a $C_{2-5}$ alkoxycarbonyl group, a piperidino group which is substituted with a mono- or di-$C_{2-7}$ alkylaminocarbonyl group, a piperidino group which is substituted with a $C_{1-4}$ alkoxy-$C_{1-6}$ alkyl group, a piperidino group which is substituted with a $C_{1-6}$ hydroxyalkyl group and a piperidino group which is substituted with a mono- or di-$C_{1-4}$ alkylamino-$C_{1-6}$ alkyl group and its examples are 2-methylpiperidino group, 3-methylpiperidino group, 4-methylpiperidino group, 4-ethylpiperidino group, 4-methoxypiperidino group, 4-hydroxypiperidino group, 4-methoxycarbonylpiperidino group, 4-ethoxycarbonylpiperidino group, 4-dimethylaminocarbonylpiperidino group, 3-diethylaminocarbonylpiperidino group, 4 (2-methoxyethyl)piperidino group, 4-(2-hydroxyethyl)piperidino group and 4-(2-dimethylaminoethyl)piperidino group where 4-hydroxypiperidino group, 4-(2-hydroxyethyl)piperidino group, 4-ethoxycarbonylpiperidino group and 3-diethylaminocarbonylpiperidino group are more preferred.

The substituted piperazin-1-yl group means a piperazin-1-yl group, a piperazin-1-yl group which is substituted with a $C_{1-4}$ alkyl group, a piperazin-1-yl group which is substituted with a cycloalkyl group having 4 to 8 ring members, a piperazin-1-yl group which is substituted with a $C_{1-4}$ alkoxy-$C_{1-4}$ alkyl group, a piperazin-1-yl group which is substituted with a $C_{1-6}$ hydroxyalkyl group, a piperazin-1-yl group which is substituted with a mono- or di-$C_{1-4}$ alkylamino-$C_{1-6}$ alkyl group, a piperazin-1-yl group which is substituted with a pyrrolidin-1-yl-$C_{1-6}$ alkyl group, a piperazin-1-yl group which is substituted with a morpholinocarbonyl-$C_{1-6}$ alkyl group, a piperazin-1-yl group which is substituted with a $C_{2-6}$ alkanoyl group, a piperazin-1-yl group which is substituted with a phenyl group and a piperazin-1-yl group which is substituted with a pyridyl group and its examples are 2-methylpiperazin-1-yl group, 3-methylpiperazin-1-yl group, 4-methylpiperazin-1-yl group, 4-ethylpiperazin-1-yl group, 4-cyclohexylpiperazin-1-yl group, 4-(2-methoxyethyl)piperazin-1-yl group, 4-(2-hydroxyethyl)piperazin-1-yl group, 4-(2-dimethylaminoethyl)piperazin-1-yl group, 4-(2-pyrrolidin-1-yl-ethyl)piperazin-1-yl group, 4-(1-morpholinocarbonylmethyl)piperazin-1-yl group and 4-phenylpiperazin-1-yl group where 4-methylpiperazin-1-yl group, 4-ethylpiperazin-1-yl group, 4-cyclohexylpiperazin-1-yl group, 4-(2-hydroxyethyl)piperazin-1-yl group, 4-(2-dimethylaminoethyl)piperazin-1-yl group, 4-(2-pyrrolidin-1-yl-ethyl)piperazin-1-yl group, 4-(morpholinocarbonylmethyl)piperazin-1-yl group, 4-acetylpiperazin-1-yl group, 4-phenylpiperazin-1-yl group and 4-(2-pyridyl)piperazin-1-yl group are more preferred.

"$C_{x-y}$" means that a group thereafter has x to y carbon atoms.

The halogen atom is fluorine atom, chlorine atom, bromine atom or iodine atom.

The $C_{1-4}$ and $C_{1-6}$ alkyl groups mean a linear or branched alkyl group having 1-4 and 1-6 carbon atom(s), respectively.

The $C_{1-4}$ alkoxy group means a linear or branched alkoxy group having 1 to 4 carbon(s).

The $C_{2-5}$ alkoxycarbonyl group means a substituent in a compounded form of a linear or branched alkoxy group having 1 to 4 carbon(s) with carbonyl group.

The mono- or di-$C_{2-7}$ alkylaminocarbonyl group means a substituent in a compounded form of an amino group, which is substituted with one or two linear or branched alkyl group(s) having 1 to 6 carbon (s), with carbonyl group.

The $C_{1-4}$ alkoxy-$C_{1-4}$ alkyl group means a substituent in a compounded form of a linear or branched alkoxy group having 1 to 4 carbon(s) with a linear or branched alkyl group having 1 to 4 carbon(s).

The $C_{1-6}$ hydroxyalkyl group means a linear or branched alkyl group having 1 to 6 carbon(s) substituted with hydroxyl group.

The mono- or di-$C_{1-4}$ alkylamino-$C_{1-6}$ alkyl group means a substituent in a compounded form of an amino group, which is substituted with one or two linear or branched alkyl group(s) having 1 to 4 carbon(s), with a linear or branched alkyl group having 1 to 6 carbon (s).

The cycloalkyl group having 4 to 8 ring members means cyclobutyl group, cyclopentyl group, cyclohexyl group, cycloheptyl group and cyclooctyl group.

The pyrrolidin-1-yl-$C_{1-6}$ alkyl group means a linear or branched alkyl group having 1 to 6 carbon(s) substituted with a pyrrolidin-1-yl group.

The morpholinocarbonyl-$C_{1-6}$ alkyl group is a linear or branched alkyl group having 1 to 6 carbon(s) substituted with a morpholinocarbonyl group.

The pharmaceutically acceptable salt is a salt with alkaline metal, alkaline earth metal, ammonium, alkylammonium, etc. and a salt with mineral acid or organic acid. Its examples are sodium salt, potassium salt, calcium salt, ammonium salt, aluminum salt, triethylammonium salt, acetate, propionate, butyrate, formate, trifluoroacetate, maleate, tartrate, citrate, stearate, succinate, ethylsuccinate, lactobionate, gluconate, glucoheptonate, benzoate, methanesulfonate, ethanesulfonate, 2-hydroxyethanesulfonate, benzenesulfonate, p-toluenesulfonate, laurylsulfate, malate, aspartate, glutamate, adipate, a salt with cysteine, a salt with N-acetyl-cysteine, hydrochloride, hydrobromide, phosphate, sulfate, hydroiodide, nicotinate, oxalate, picrate, thiocyanate, undecanoate, a salt with acrylic acid polymer and a salt with carboxyvinyl polymer.

(3) Imidazole Derivatives.

The imidazole derivatives described in Nakamura T et al., *Bioorg Med Chem Lett.* 14:5305-5308, 2004 and Nakamura T et al., *Bioorg Med Chem Lett.* 14:333-336, 2004 as 20-HETE synthesis inhibitors can be used in the present invention. For the purpose of the present invention, these inhibitors are defined as imidazole derivative 20-HETE synthesis inhibitors and include compounds 1-18 in Table 1.

TABLE 1

| The number in the left column is the compound number and the structure of the corresponding compound is shown in the right column. | |
|---|---|
| 1 | 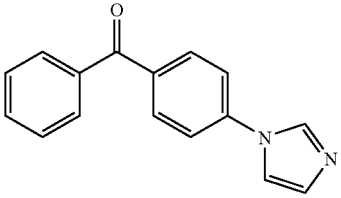 [SMILES: O=C(c1ccccc1)c1ccc(-n2ccnc2)cc1] |
| 2 | 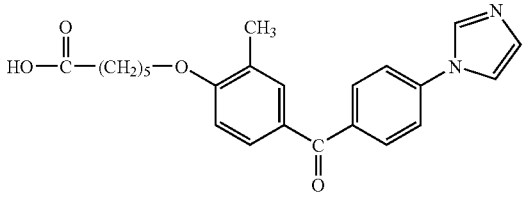 |
| 3 | 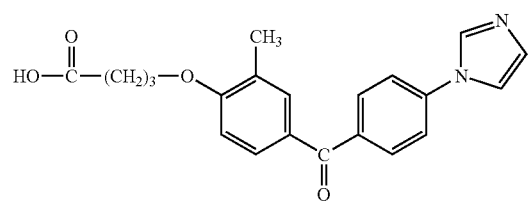 |
| 4 | 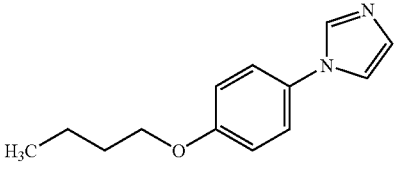 [SMILES: CCCCOc1ccc(-n2ccnc2)cc1] |
| 5 | 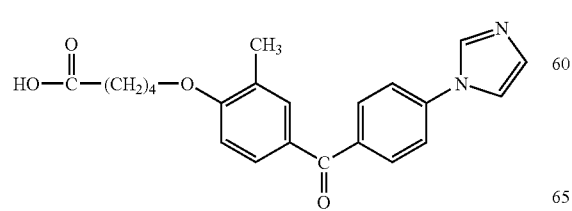 |
| 6 | 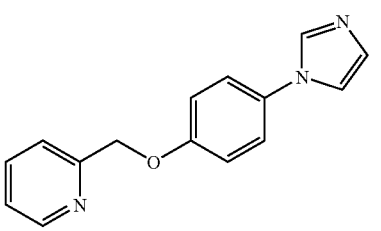 [SMILES: c1ccc(COc2ccc(-n3ccnc3)cc2)nc1] |
| 7 | 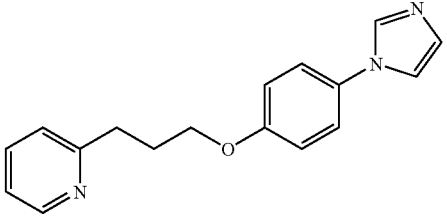 [SMILES: c1ccc(CCCOc2ccc(-n3ccnc3)cc2)nc1] |
| 8 | 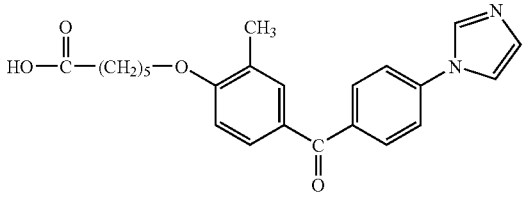 |
| 9 | 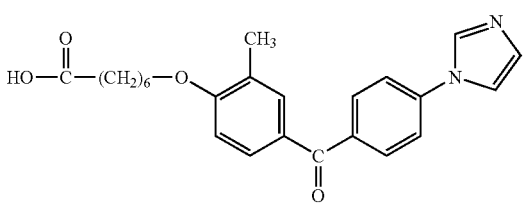 |
| 10 | 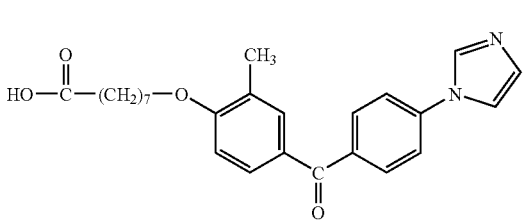 |

TABLE 1-continued

The number in the left column is the compound number and the structure of the corresponding compound is shown in the right column.

11 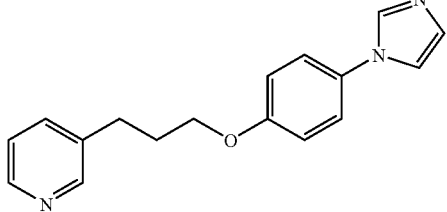

12 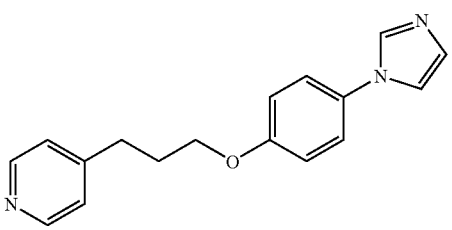 [SMILES: c1cc(CCCOc2ccc(-n3ccnc3)cc2)ccn1]

13 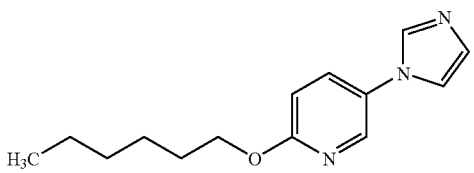 [SMILES: CCCCCCOc1ccc(-n2ccnc2)cn1]

14 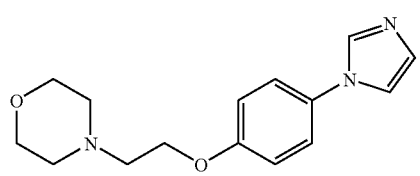 [SMILES: c1cn(-c2ccc(OCCN3CCOCC3)cc2)cn1]

15 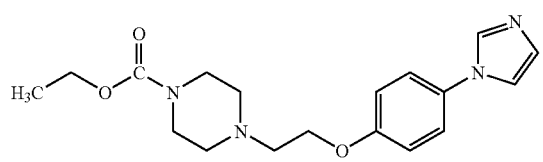 [SMILES: CCOC(=O)N1CCN(CCOc2ccc(-n3ccnc3)cc2)CC1]

16 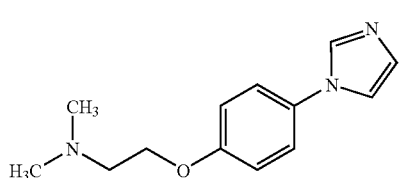

17 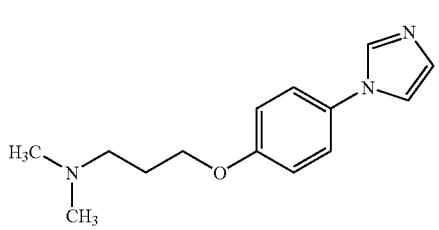 [SMILES: CN(C)CCCOc1ccc(-n2ccnc2)cc1]

18 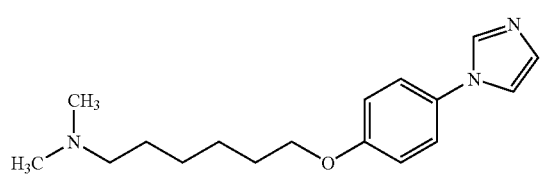 [SMILES: CN(C)CCCCCCOc1ccc(-n2ccnc2)cc1]

(4) Pyrazole and Isoxazole Derivatives.

The pyrazole and isoxazole derivatives described in Nakamura T et al., *Bioorg Med Chem.* 12:6209-6219, 2004 and Nakamura T et al., *J Med Chem.* 46:5416-5427, 2003 as 20-HETE synthesis inhibitors can be used in the present invention. For the purpose of the present invention, these inhibitors are defined as pyrazole and isoxazole derivative 20-HETE synthesis inhibitors and include compounds 19-49 in Table 2.

TABLE 2

The number in the left column is the compound number and the structure of the corresponding compound is shown in the right column.

19  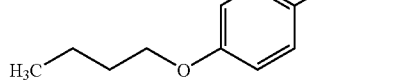

20 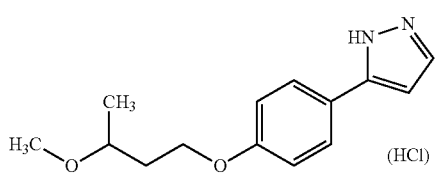 (HCl)

21 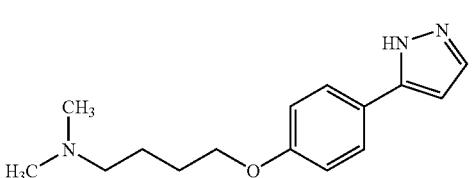

22 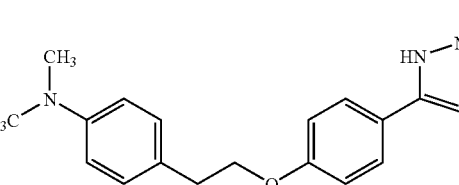

23 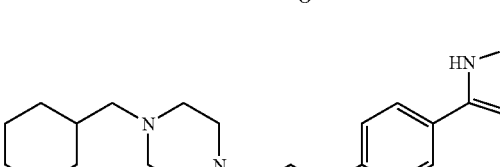  (3HCl)

24  (p-TsOH)

25 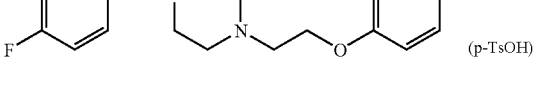 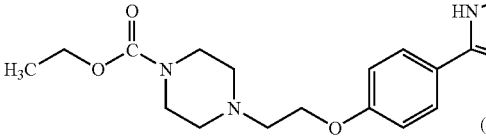 (2HCl)

TABLE 2-continued

The number in the left column is the compound number and the structure of the corresponding compound is shown in the right column.

TABLE 2-continued

The number in the left column is the compound number and the structure of the corresponding compound is shown in the right column.

| 43 | 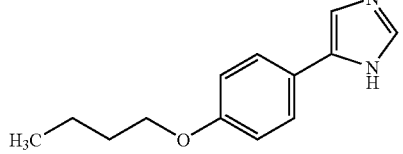 |
| 44 | 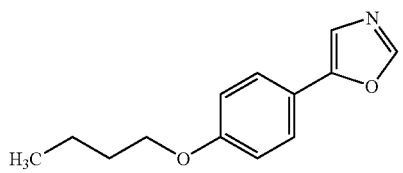 [SMILES: CCCCOc1ccc(-c2cnco2)cc1] |
| 45 | 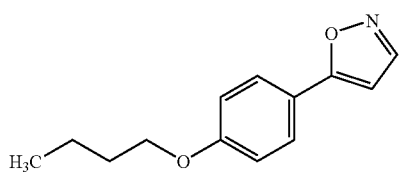 |
| 46 | 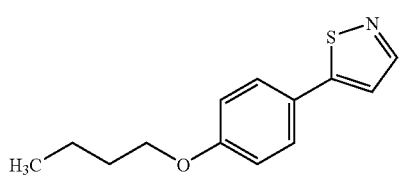 [SMILES: CCCCOc1ccc(-c2ccns2)cc1] |
| 47 | 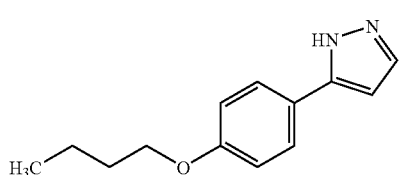 |
| 48 | 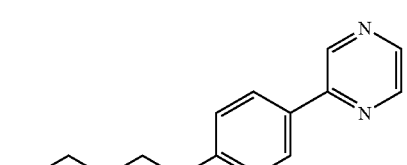 |
| 49 | 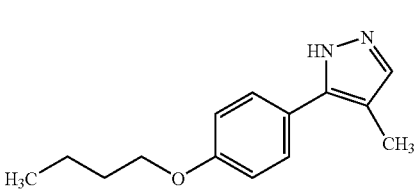 [SMILES: CCCCOc1ccc(-c2[nH]ncc2C)cc1] |

Antibodies

Antibodies (monoclonal or polyclonal) against a 20-HETE synthesizing enzyme can also be used to inhibit 20-HETE synthesis as it has been shown in general that an antibody can block the function of a target protein when administered into the body of an animal (Dahly, A. J., *FASEB J.* 14:A133, 2000; Dahly, A. J., *J. Am. Soc. Nephrology* 11:332A, 2000). The DNA and protein amino acid sequences of all known members of the CYP4A and CYP4F families are published and available. A skilled artisan can thus make antibodies including humanized antibodies to a 20-HETE synthesis enzyme. For example, antibodies against CYP4A1 and CYP4A10 have been made and shown to be capable of inhibiting the enzymatic activity of CYP4A1 and CYP4A10 (Amet, Y. et al., *Biochem Pharmacol.* 54(8): 947-952, 1997; Amet, Y. et al., *Biochem. Pharmacol.* 53(6): 765-771, 1997; Amet, Y. et al., *Alcohol Clin. Exp. Res.* 22(2): 455-462, 1998). Certain such antibodies are also commercially available (e.g., anti-CYP4A1 is available from Gentest Corp., Woburn, Mass.).

20-HETE Antagonists

Another suitable way to inhibit 20-HETE activity in a human or non-human mammal is to administer a 20-HETE antagonist to the human or non-human mammal. All known 20-HETE antagonists can be used. These include those disclosed in U.S. Pat. No. 6,395,781; Yu M et al., *Eur J Pharmacol.* 486:297-306, 2004; Yu M et al., *Bioorg Med Chem.* 11:2803-2821, 2003; and Alonso-Galicia M et al., *Am J Physiol.* 277:F790-796, 1999, all of which are herein incorporated by reference in their entirety. For example, 20-HETE antagonists defined by the following formula (IV) as provided in U.S. Pat. No. 6,395,781 can be used in the present invention:

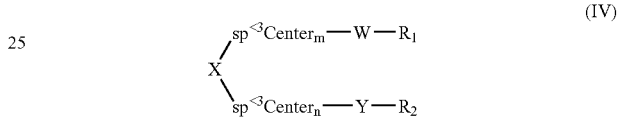

(IV)

wherein $R_1$ is selected from the group consisting of carboxylic acid, phenol, amide, imide, sulfonamide, sulfonamide, active methylene, 1,3-dicarbonyl, alcohol, thiol; amine, tetrazole and other heteroaryl groups;

$R_2$ is selected from the group consisting of carboxylic acid, phenol, amide, imide, sulfonamide, sulfonamide, active methylene, 1,3-dicarbonyl, alcohol, thiol, amine, tetrazole and other heteroaryl;

W is a carbon chain ($C_1$ through $C_{25}$) and may be linear, cyclic, or branched and may comprise heteroatoms;

Y is a carbon chain ($C_1$ through $C_{25}$) and may be linear, cyclic, or branched and may comprise heteroatoms;

$sp^{<3}$ Center is selected from the group consisting of vinyl, aryl, heteroaryl, cyclopropyl, and acetylenic moieties;

X is an alkyl chain that may be linear, branched, cyclic or polycyclic and may comprise heteroatoms;

m is 0, 1, 2, 3, 4 or 5; and n is 0, 1, 2, 3, 4 or 5.

Preferably, a 20-HETE antagonist defined by the above formula (IV) contains a length of 19-21 carbons, has a carboxyl or other ionizable group at either $R_1$ or $R_2$, has a pair of double bonds or other functional group at a distance equal to 14-15 carbons from the ionizable group and does not have a hydroxyl group on the 20-21 carbon at either $R_1$ or $R_2$ (U.S. Pat. No. 6,395,781).

In one form, the present invention contemplates the use of one or more of the following 20-HETE antagonists: 19 hydroxynonadecanoic acid, 20-hydroxyeicosanoic acid, 20-hydroxyeicosa-6(Z),15(Z)-dienoic acid (WIT-002), N-methylsulfonyl-20-hydroxyeicosa-6(Z),15(Z)-dienamide, and 19 hydroxynonadeca-5(Z),8(Z),11(Z),14(Z) tetraenoic acid.

The present invention is not limited by any route of administration. Suitable routes of administration of a 20-HETE synthesizing enzyme inhibitor or a 20-HETE antagonist include but are not limited to oral administration, intravenous administration, intraarterial administration, subcutaneous administration, intramuscular administration, intraperitoneal administration, and direct delivery into the kidney or liver/bile duct.

The invention will be more fully understood upon consideration of the following non-limiting examples.

EXAMPLE 1

The Effect of 20-HETE Synthesizing Enzyme Inhibitors and 20-HETE Antagonist on the Proliferation of REC11 Cells REC11 cystic cell line is a conditionally immortalized epithelial collecting tubule (CT) cell line derived from the cystic kidneys of the BPK mouse model of human ARPKD crossed to the ImmortoMouse. The BPK mouse as a human ARPKD model has been described in Nauta J. et al., Pediatr Nephrol 1993, 7:163-172 and Nauta J. et al., Pediatr Res 1995, 37:755-763. The procedures for immortalization, cell isolation, cell culture and the complete phenotypic characterization of this cell line have been described in detail in Sweeney W. E. et al., Am J Physiol C Physiol 2001, 281: C1695-705. All analysis and experiments were performed on REC11 cells grown for a minimum 6 days under non-permissive conditions to eliminate residual Large T.

Proliferation of REC11 cells was stimulated by exposure of the cells for 6 hours with EGF (25 ng/ml). Next, the cells were treated with vehicle, HET0016 (10 µM, a 20-HETE synthesis inhibitor), HET0016 (20 µM), DDMS (10 µM, a 20-HETE synthesis inhibitor), or WIT-002 (10 µM, a 20-HETE antagonist) for 36 hrs, pulsed with BrdU, and then stained for BrdU labeled cells to determine the degree of cell proliferation. As shown in FIG. 1, compared to the rate of proliferation seen in vehicle treated cells (column A), cells treated with HET0016 (10 µM) (column B) reduced proliferation by 66% (p<0.025). Cells treated with a higher dose of HET0016 (20 µM) (column C) reduced proliferation by 75% (p<0.020). Cells treated with another chemically dissimilar inhibitor of the synthesis of 20-HETE, DDMS (10 µM) (column D), reduced proliferation by 47% (p<0.05). Cells treated with WIT-002 (10 µM) (column E) reduced proliferation by 25%.

EXAMPLE 2

HET0016 Inhibits EGF Receptor (EGFR) Phosphorylation in Cystic Epithelium But not in Normal Renal Epithelial Cells REC11 cystic cell line is a conditionally immortalized epithelial collecting tubule (CT) cell line derived from the cystic kidneys of the BPK mouse model of human ARPKD crossed to the ImmortoMouse. The BPK mouse as a human ARPKD model has been described in Nauta J. et al., Pediatr Nephrol 1993, 7:163-172 and Nauta J. et al., Pediatr Res 1995, 37:755-763. The procedures for immortalization, cell isolation, cell culture and the complete phenotypic characterization of this cell line have been described in detail in Sweeney W. E. et al., Am J Physiol C Physiol 2001, 281: C1695-705. All analysis and experiments were performed on REC11 cells grown for a minimum 6 days under non-permissive conditions to eliminate residual Large T. REC12 cell line is a conditionally immortalized epithelial collecting tubule (CT) cell line derived from the wild-type Balb/C littermates. The Balb/C is the strain of mice in which the BPK mutation arose (Nauta J. et al., Pediatr Nephrol 1993, 7:163-172 and Nauta J. et al., Pediatr Res 1995, 37:755-763).

Figure 2:
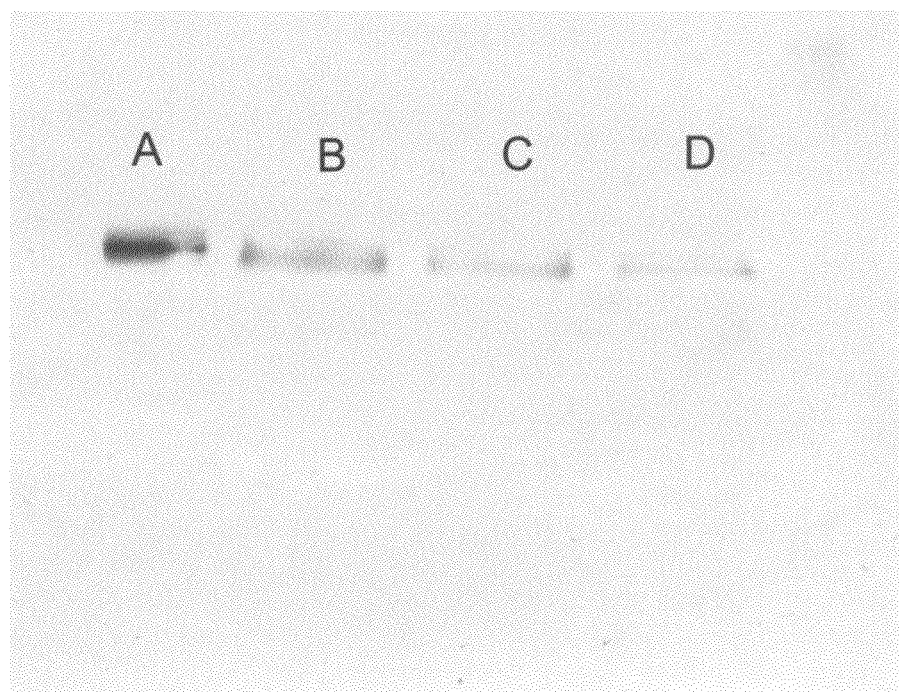
FIG. 2 shows the effect of HET0016 on the phosphorylation state of the EGF receptor in cystic renal epithelial cells (REC11) derived from the BPK mouse and the lack of an effect of HET0016 on the phosphorylation of the EGF receptor in normal renal epithelial cells derived from the kidney of a normal BALB/c control mouse.

REC11 cells (FIG. 2, lanes A and B) and control renal epithelial cells (REC12 cells: FIG. 2, lanes C and D) were grown for 10 days. Next, the cells were exposed to vehicle (lanes A and C) or 10 µM HET0016 (lanes B and D) and then harvested for assessment of the expression of phosphorylated EGFR by Western Blot analysis. As shown in FIG. 2, HET0016 reduced the phosphorylation of EGFR in REC11 cystic renal epithelial cells but not in normal renal epithelial cells (REC12 cells).

EXAMPLE 3

20-HETE Synthesis Inhibitor Reduces Kidney Mass and Quantitative Morphometric Indices of Cystic Disease in the BPK Mouse, a Well-Characterized Model of ARPKD In this example, we show that 20-HETE is a key mitogen in renal cystic disease, utilizing the well-characterized BPK mouse model of autosomal recessive polycystic kidney disease (ARPKD). Chronic daily administration of a 20-HETE synthesis inhibitor, HET-0016 (10 mg/kg/day) markedly reduced kidney size, the primary determinant of therapeutic efficacy, from 1.08 g to 0.43 g in BPK mice. Principal cells isolated from conditionally immortalized cystic BPK and non-cystic Balb/C (+/+) mice were studied to further characterize the role of 20-HETE in proliferation of these cells. Cystic BPK cells exhibited significantly elevated levels of cytochrome P4504a12 (Cyp4a12) mRNA and higher production of 20-HETE as compared to non-cystic Balb/C controls. Lentiviral vectors expressing Cyp4a10 and Cyp4a12 were generated, and serially transduced into non-cystic Balb/C cells at MOI 40. Under non-permissive conditions, genetically modified non-cystic Balb/C cells over-expressing either Cyp4a10 or Cyp4a12 exhibited a 5-fold increase in cell proliferation as compared to Balb/C cells transduced with the vector alone (p<0.001), simulating the phenotype of cystic BPK cells. Moreover, the blockade of 20-HETE synthesis using HET-0016 (10 µM) completely abolished the increased cell proliferation in the Balb/C cells over-expressing Cyp4a12. These findings establish that cystic renal epithelial cells exhibit elevated production of 20-HETE and 20-HETE is a mediator of epithelial cell proliferation leading to the pathogenesis of renal cyst formation.

Materials and Methods

Chemicals and Reagents:

N-hydroxy-N'-(4-n-butyl-2-methylphenyl)-formamidine (HET-0016) was purchased from BIOMOL International, LP (Plymouth Meeting, Pa.).

ImmortoMouse×Balb/C Polycystic Kidney (BPK) Mice:

This study was conducted using "immortalized" BPK mice as previous described by Sweeney W E et al. (*Am J Physiol Cell Physiol,* 281:C1695-705, 2001). In brief, BPK female heterozygotes (bpk$^{+/-}$) were bred with H-2k$^b$-ts-A58 transgenic males. Compound heterozygotes (bpk$^{+/-}$; H-2K$^b$-ts-A58$^{+/-}$) were identified by PCR and backcrossing to produce cystic offspring. Compound heterozygotes were mated to generate cystic (bpk$^{-/-}$; H-2K$^b$-ts-A58$^{+/\pm}$) and non-cystic (bpk$^{-/-}$; H-2K$^b$-ts-A58$^{+/\pm}$) offspring carrying at least one copy of the Immorto transgene (bpk$^{-/-}$; H-2K$^b$-ts-A58$^{+/\pm}$). All of the mice were genotyped for the H-2K$^b$-ts-A58 transgene by PCR analysis of DNA extracts from tail sections as described in Takacs-Jarrett M et al. *Am J Physiol,* 275:F802-11, 1998.

Immunohistology of Cystic BPK Kidneys with and without 20-HETE Inhibition:

Kidney and liver tissues were harvested for qualitative analysis as described in Sweeney W E et al. (Kidney Int, 57:33-40, 2000) at postnatal day 21. Briefly, kidney and liver were fixed in 4.0% paraformaldehyde in phosphate buffer (pH 7.4) for 30 min at 4° C. Tissues were then washed, dehydrated through a graded series of acetone, and fixed in Immunobed embedding medium (Polysciences, Warrington, Pa.). Sections were cut at 4 µm, mounted on glass slides, and stained with hematoxylin or lectins staining the proximal tubule [Lotus tetragonobulus agglutinin (LTA)] and collecting tubule [Dolichol biflorus agglutinin (DBA)]. Segmental nephron cyst localization was characterized by light microscopy, and cystic lesions were quantitated by a morphometric index as described in Nakanishi K et al. (J Am Soc Nephrol, 12:719-25, 2001), Richards W G et al. (J Clin Invest, 101:935-9, 1998), Sweeney W E et al. (Kidney Int, 57:33-40, 2000), and Sweeney W E et al. (Kidney Int, 64:1310-9, 2003).

Figure 3:
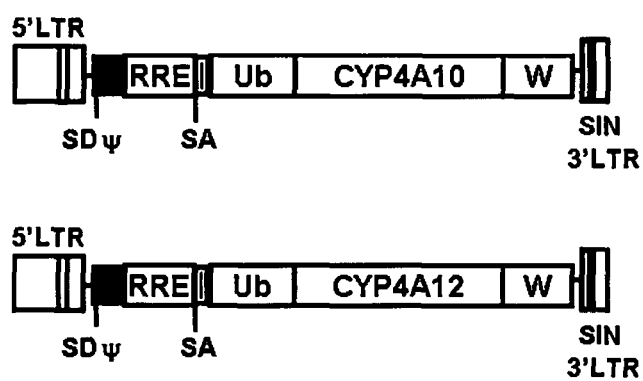
FIG. 3 provides a schematic showing of lentiviral vector transfer plasmid. The lentiviral vector transfer plasmid was cloned with the human ubiquitin (Ub) promoter driving the expression of the full-length murine cytochrome P450 4A10 (Cyp4a10) and 4A12 (Cyp4a12) cDNA. RRE=rev-responsive element; W=woodchuck post-regulatory element; SD=splice donor; SA=splice acceptor; ψ=packaging signal; 3' SIN LTR=3' self-inactivating long-terminal repeat; grey box=central polypurine tract sequence.

Construction of CYP4A-Expressing Lentiviral Vector Transfer Plasmid:

Murine full-length Cyp4a10 (cDNA clone MGC:58977) and Cyp4a12 (cDNA clone MGC:25972) cDNA clones were purchased from ATCC (Manassas, Va.). The backbone lentiviral vector transfer plasmid used in these studies was described in Park F et al. Mol Ther, 4:164-73, 2001. In brief, the lentiviral vector transfer plasmid contained debilitated 3' long-terminal repeats (LTR), a small 118 bp segment from the pol gene known as the central polypurine tract sequence (cppt) and the woodchuck post-regulatory element (WPRE) as shown in FIG. 3. For the cloning of the Cyp4a10-expressing transfer plasmid, pHR(+)c.Ub.GFP.R(−)W(+) was double digested with KpnI and XbaI to remove the GFP cDNA, and replaced with the XbaI/KpnI fragment containing the Cyp4a10 cDNA. The final construct was named pHR(+)c.Ub.CYP4A10.R(−)W(+). For the Cyp4a12-expressing transfer plasmid, an additional XbaI/XbaI fragment containing the 3' end of the Cyp4a12 cDNA was cloned into the XbaI-digested pHR(+)c.Ub.CYP4A12(short).R(−)W(+) plasmid to make the final construct, pHR(+)c.Ub.CYP4A12.R(−)W(+).

Packaging and Envelope Pseudotype Plasmids:

pCMVΔR8.74 is the packaging plasmid that provides the expression of the gag-pol, tat and rev genes, and the viral accessory genes have been deleted or attenuated as described by Dull T et al. (J Virol, 72:8463-71, 1998). pMD.G is the envelope plasmid and encodes the vesicular stomatitis virus G protein as described in Naldini L et al. Science, 272:263-7, 1996.

Lentiviral Vector Production:

Modified lentiviral vectors were produced by transient triple-plasmid transfection of 293T cells as described in Park F (Hum Gene Ther, 14:1489-94, 2003), Park F et al. (Nat Genet, 24:49-52, 2000), Park F et al. (Mol Ther, 8:314-23, 2003) and Qian Z et al. (Mol Ther, 13:694-704, 2006). The advanced third-generation lentiviral vectors were produced by a similar manner as the three-plasmid system, but the following amounts of plasmid DNA were used: 10 µg transfer plasmid, 6.5 µg packaging plasmid, and 3.5 µg envelope plasmid. Conditioned media were collected at 48 hrs, filtered and frozen at −80° C. Single channel FACS analysis (Becton Dickinson, Franklin Lakes, N.J.) was performed on EGFP-expressing lentiviral vectors and analyzed with the CellQuest program (Version 3.1f; Becton Dickinson) to determine lentiviral vector titer.

Non-Cystic Balb/C (+/+) and Cystic BPK Renal Epithelial Cell Isolations:

The renal epithelial cell isolation was performed on postnatal day 14 in non-cystic Balb/C (+/+) and cystic BPK mice as described in Sweeney W E et al. (Am J Physiol Cell Physiol, 281:C1695-705, 2001) and Takacs-Jarrett M et al. (Am J Physiol, 275:F802-11, 1998). The renal epithelial cells were maintained in a serum-free defined medium consisting of a 1:1 mixture of Dulbecco's modified Eagle's medium and Ham's F-12 medium, supplemented with insulin ($8.3 \times 10^{-7}$ M), prostaglandin $E_1$ ($7.1 \times 10^{-8}$ M), selenium ($6.8 \times 10^{-9}$ M), transferrin ($6.2 \times 10^{-8}$ M), triiodothyronine ($2 \times 10^{-9}$ M), dexamethasone ($5.09 \times 10^{-8}$ M), and recombinant γ-IFN (10 U/ml; Invitrogen Corp., Carlsbad, Calif.) at 33° C. (permissive conditions). The cells were serially transduced with VSV-G pseudotyped lentiviral vectors in the presence of polybrene (8 µg/mL) on a daily basis as the cells were expanded to determine lentiviral vector transduction efficiency by FACS analysis.

In Vitro Experiments Using the Conditionally Immortalized Cell Lines:

For the cell counting experiments, the non-cystic Balb/C (+/+) and cystic BPK renal epithelial cells were seeded in 6-well dishes and changed into media lacking γ-IFN at 37° C. (non-permissive conditions) for at least 6 additional days prior to assessing any phenotypic analyses to ensure the loss of the T antigen (Sweeney W E et al. Am J Physiol Cell Physiol, 281:C1695-705, 2001). Cells were harvested by tryptic digestion and counted by light microscopy using a hemocytometer.

To determine the level of proliferation in the cystic BPK cells, chemically dissimilar inhibitors of cytochrome P450 4A (CYP4A) and 4F (CYP4F) inhibitors, specifically HET-0016 (10 and 20 µM) and DDMS (10 µM), were incubated for 36 hours with the BPK cells. Three hours prior to the harvesting of the cells, 5-bromo-2'-deoxyuridine (BrdU) at a concentration of 30 µM was added to determine the level of cell cycle inhibition. The cells were subsequently methanol fixed and BrdU-positive cells were identified by immunohistology with biotinylated monoclonal anti-BrdU antibody (Zymed, South San Francisco, Calif.). Data were expressed as the percentage of BrdU-labeled cells per 500 counted cells.

Reverse Transcription-Real Time Quantitative PCR for Cyp4a10 and Cyp4a12:

Total RNA was extracted from the cystic BPK and non-cystic Balb/C (+/+) cells using TRIzol reagent (Invitrogen Corp., Carlsbad, Calif.). The total RNA (2 µg) will be DNAse-treated with 1 Unit of RQ1 RNAse-free DNAse (Promega, Madison, Wis.) for 30 min., and the RNA will be reverse transcribed using oligo-dT primer and SuperScript III RTase (Invitrogen Corp., Carlsbad, Calif.) for 60 minutes at 42° C. Following cDNA synthesis, the RT products will be heated to 85° C. for 10 minutes and immediately placed on ice. All primers for PCR were purchased from Integrated DNA Technologies (Coralville, Iowa) using gene-specific primers for Cyp4a10, Cyp4a12 and Cyp4a14 are as follows: Cyp4a10, sense: 5'-GACAAGGACCTACGTGCTGAGG-3' (SEQ ID NO: 1), antisense: 5'-CTCATAGCAAATTGTTTCCCA-3' (SEQ ID NO:2); Cyp4a12, sense: 5'-TGAGTCCTATGAAA-GAGTGC C-3' (SEQ ID NO:3), antisense: 5'-CTGGAAGC-CCAGCAGAAGGT G-3' (SEQ ID NO:4); and Cyp4a14, sense: 5'-CCTACAA GGTACTTGGATGGT-3' (SEQ ID NO:5) and antisense, 5'-ATCATAAAGCAGGACTCG-TATA-3' (SEQ ID NO:6). Real-time quantitative PCR was performed using Stratagene 3000XP real-time PCR machine and SYBR Green reagents. The PCR reaction mixture contained 1×SYBR Green PCR master mix, 1 U Vent DNA polymerase (NEB), 50 nM forward and reverse primers, and 100-250 ng cDNA in a total reaction volume of 20 µl. Each reaction was performed at the following conditions: 95° C. for 10 minutes, 95° C. for 15 seconds, 60° C. for 1 minute, and 72° C. for 30 seconds for a total of 40 cycles. The number of cycles at which fluorescent signals reach a detection threshold set within the exponential phase of the PCR reaction ($C_t$ numbers) will be used to calculate the expression levels of genes of interest. The values are expressed as mean copies of mRNA±standard error of the mean (SEM).

Liquid Chromatography-Mass Spectrometry for 20-HETE Detection:

Microsomes were isolated from the cystic BPK and non-cystic Balb/C mouse kidneys as described by Ito O et al. (*Am J Physiol Regul Integr Comp Physiol*, 280:R822-30, 2001). For the BPK and Balb/C cells, protein lysates were harvested by homogenization and subsequent sonication of the cell pellets. For the 20-HETE production assay, the isolated protein (500 µg) was incubated in 0.5 mL of 100 mM potassium phosphate buffer containing 40 µM cold arachidonic acid and 2 mM NADPH. In some samples, the 20-HETE synthesis inhibitor, HET-0016, was added at a concentration of 1 µM. The reaction was incubated at 37° C. and equilibrated with 100% $O_2$ for 30 minutes. The reaction was stopped by acidification to pH 3.5 with 1M formic acid. The lipids were extracted in the presence of 20-HETE-d6 (2 ng) using 3:1 ethyl acetate:water and dried down under nitrogen. The samples were reconstituted in 1:1 methanol:water and the production of 20-HETE was measured using a liquid chromatograph-triple quadrupole mass spectrometer (ABI 3000, Applied Biosystems, Inc., Foster City, Calif.) as described in Williams J M et al. Hypertension, 49:687-94, 2007.

Statistical Analysis:

The results are calculated as mean±SEM. The significance of differences between groups was examined by a one- and two-way ANOVA with Prism 4.0 software (Graph Pad Software) followed by a Bonferroni post-hoc test. The statistical significance was defined as $p<0.05$.

Results

Effects of Chronic Administration of 20-HETE on Cystogenesis in the BPK Mice:

To investigate the effect of cytochrome P450 4A and 4F blockade in vivo, we studied the well-characterized BPK murine model of ARPKD (Nakanishi K et al. *J Am Soc Nephrol*, 12:719-25, 2001). The BPK mouse model features the reliable and consistently aggressive renal phenotype similar to human disease. In addition, therapeutic interventions can be readily screened in BPK mice due to the relatively short life span following birth (21-24 days) (Guay-Woodford LM *Am J Physiol Renal Physiol*, 285:F1034-49, 2003).

Figure 4:
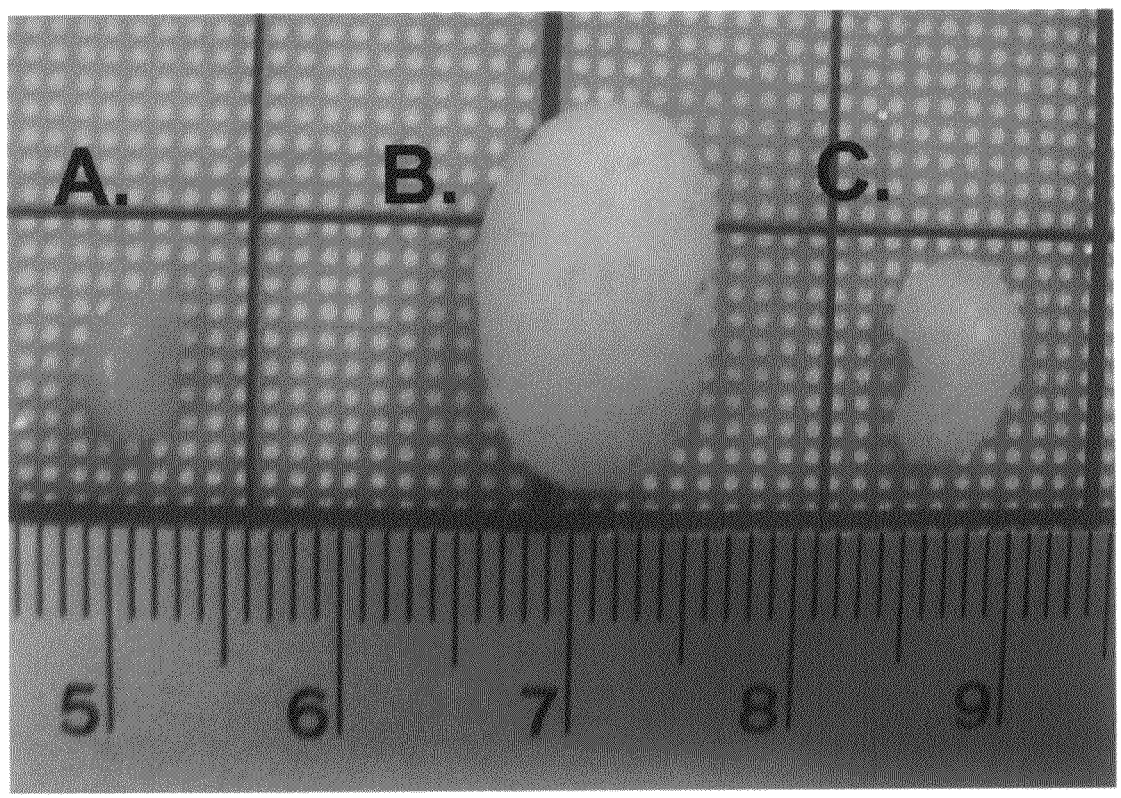
FIG. 4 shows the effect of 20-HETE inhibition on kidney mass in a mouse model of ARPKD. HET-0016 (10 mg/kg/day), a specific inhibitor of 20-HETE synthesis, was administered daily to normal Balb/C and BPK mice beginning at post-natal day 7 and ending on day 20. Mice were sacrificed on day 21 and kidneys were harvested for analysis. Representative kidneys are shown from (A) normal (vehicle-treated) Balb/C mice, (B) cystic BPK mice treated with vehicle and (C) cystic BPK mice treated with HET-0016 (10/mg/kg/day i.p.).

We administered HET-0016 (10 mg/kg/day), a specific 20-HETE synthesis inhibitor, intraperitoneally on a daily basis from post-natal day 7 to post-natal day 20. On day 21, the mice were sacrificed and the kidneys analyzed. As shown in FIG. 4, there was an expected, marked increase in the size of vehicle-treated cystic BPK kidneys (B) compared to non-cystic Balb/C kidneys (A). The kidneys from BPK mice treated with HET-0016 (C) were dramatically smaller than the vehicle-treated BPK mice (B). As shown in Table 3, the whole kidney/body weight ratio (KW/BW) averaged 1.3 in normal (vehicle-treated) Balb/C mice compared to 20.0 in the cystic BPK mice. Chronic blockade of 20-HETE synthesis lowered the KW/BW ratio to 9.4 in the HET-0016 treated BPK mice (Table 3). HET-0016 dramatically reduced the kidney size of BPK HET-0016 treated animals by 56% ($p<0.02$) and KW/BW ratio by 53% ($p<0.01$) while the reduction in body weight was not statistically significant. These data, in conjunction with the unchanged kidney weight, body weight and KW/BW ratio of Balb/C HET-0016 treated vs Balb/C vehicle treated, demonstrate that HET-0016 specifically targets proliferation in cystic renal epithelial cells. HET-0016 does not appear to affect normal renal tissue when administered in vivo.

TABLE 3

|  | Balb/c (+/+) (Vehicle) n = 3 | Balb/c (+/+) (HET-0016) n = 3 | BPK (−/−) (Vehicle) n = 3 | BPK (−/−) (HET-0016) n = 3 |
|---|---|---|---|---|
| Body weight (g) | 10.6 ± 1.0 | 10.5 ± 1.3[#] | 10.8 ± 1.0 | 10.3 ± 1.0[¥] |
| Kidney Weight (g) | 0.13 ± 0.02 | 0.13 ± 0.02[#] | 2.20 ± 0.3 | 0.97 ± 0.32** |
| KW/BW (%) | 1.3 ± 0.1 | 1.3 ± 0.2[#] | 20.0 ± 2.0 | 9.4 ± 3.3** |

Figure 5:
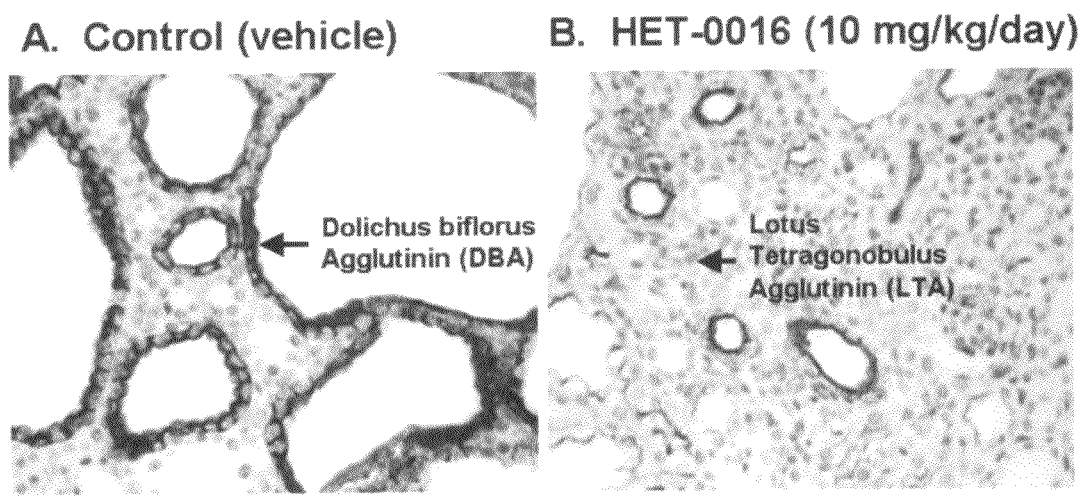
FIG. 5 shows immunohistochemical analyses of cyst formation in the mouse kidney following chronic HET-0016 administration in vivo. The localization of cyst development was determined in post-natal day 21 kidneys from BPK mice treated with (A) vehicle and (B) chronic treatment with HET-0016 (10 mg/kg/day) beginning on post-natal day 7 and ending on day 20. As shown in (A), large collecting tubule cysts, which were labeled with a Dolichol biflorus agglutinin (DBA), a collecting duct lectin, were found in the BPK kidneys treated with vehicle. There was a dramatic reduction in the DBA-labeled collecting tubule cysts with a concomitant increase in the retention of Lotus tetragonobulus agglutinin (LTA) labeled proximal cysts (brown), which is an indicator of early stages of cystic disease.

Balb/c Vehicle treated vs. Balb/c Treated (HET-0016);
BPK Treated (HET-0016) vs BPK (Vehicle);
BPK Treated (HET-0016) vs. BPK (Vehicle)
[#]NS (not significant)
[¥]NS
**$p < 0.02$ Histological examination of the kidneys from the control (vehicle-treated) and HET-0016 treated BPK mice demonstrated marked reductions in the size and number of renal cysts (FIG. 5). In the cystic BPK mice, the cysts were increased in both number and size (FIG. 5A) compared to the BPK mouse kidneys treated with HET-0016 (10 mg/kg/day; FIG. 5B). For untreated cystic animals, the collecting tubule cystic index (CI) was 4.7+/−0.6 (n=41), which includes current and historical data over the years, but there was a significant reduction ($p<0.001$) in the CI following treatment with HET-0016 to 1.93+/−0.2 (n=4). These data from the histology of the mouse kidneys clearly demonstrate that the reduction in kidney mass in the HET-0016 treated mice was attributed to the decreased number and size of the cysts.

Figure 6:
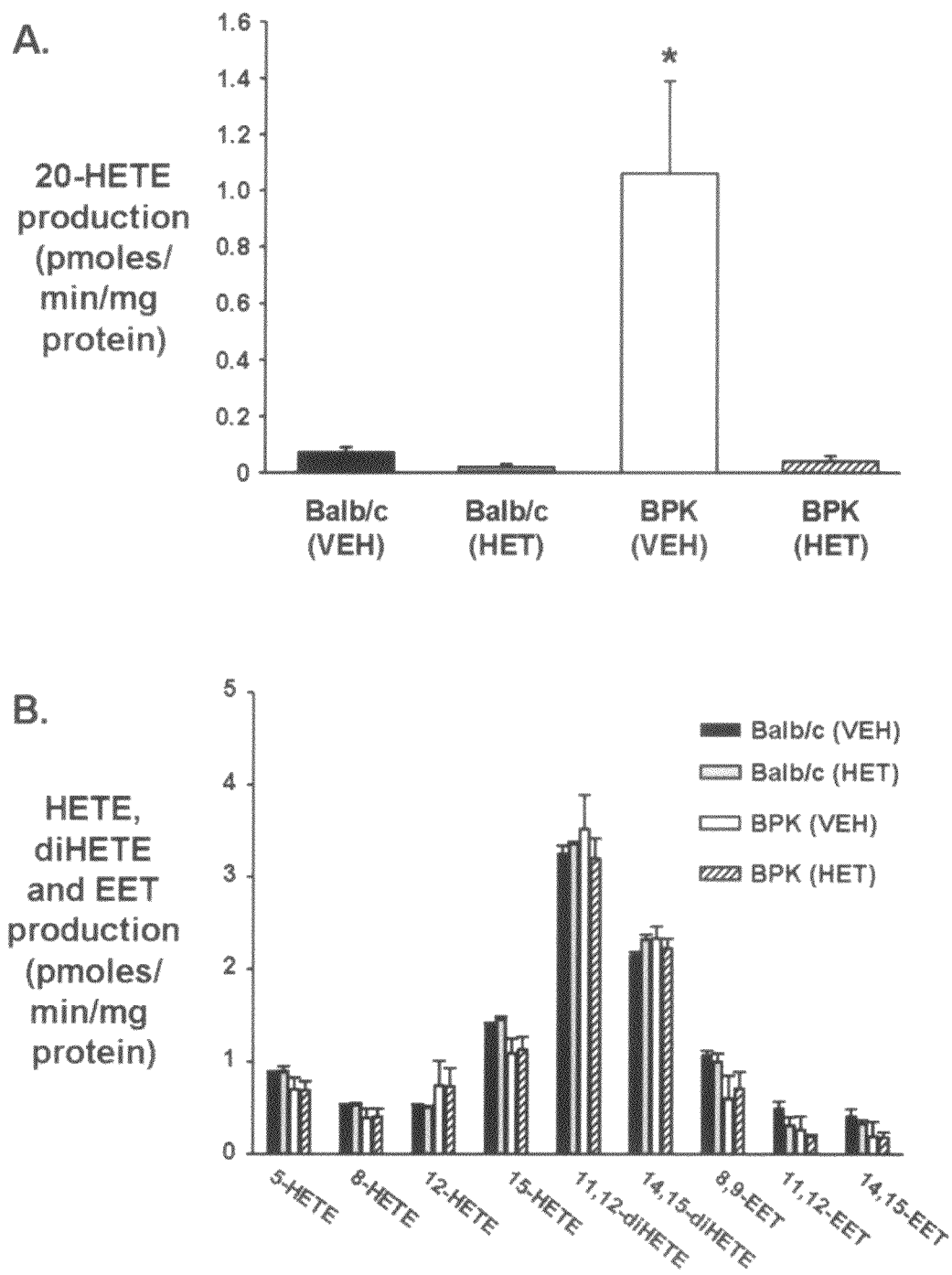
FIG. 6 shows production of 20-HETE in cystic and non-cystic mouse kidneys. HET-0016, a specific inhibitor of cytochrome P450 4A and 4F isoforms, was administered at a dose of 10 mg/kg/day i.p. to non-cystic Balb/C and cystic BPK mice 2 hours prior to sacrifice between post-natal days 7 to 21. Kidneys were harvested and microsomal protein was isolated for 20-HETE production assay in vitro. Lipids were extracted using ethyl acetate and water, and the final samples were analyzed to determine the level of 20-HETE production as well as other metabolites of arachidonic acid using liquid chromatography-quadruple mass spectroscopy (LC-MS). (A) demonstrated the 20-HETE production with vehicle (VEH) or in the presence of HET-0016 (HET; 10 mg/kg) between cystic (BPK) and non-cystic (Balb/C) mice. * $P<0.05$ significance between the BPK versus other groups. (B) demonstrated the eicosanoid profile of other arachidonic acid metabolites in the presence and absence of HET-0016 (10 mg/kg) in the cystic (BPK) and non-cystic (Balb/C) mice. n=2-3 mice/group.

To further examine the biological role of 20-HETE in the epithelial cell proliferation, post-natal day 7, 10 or 21 day old BPK mice were treated with an intraperitoneal injection of vehicle or HET-0016 (10 mg/kg/day) 2 hours prior to sacrifice at which point the kidneys were removed for measurement of 20-HETE synthesis. As shown in FIG. 6A, the production of 20-HETE was significantly higher ($P<0.05$) in the renal BPK microsomes (1.06±0.33 pmoles/min/mg protein; n=3) compared to the levels detected in the non-cystic Balb/C mouse microsomes (0.07±0.01 pmoles/min/mg protein; n=3). Administration of HET-0016 (10 mg/kg/day) selectively inhibited the formation of 20-HETE by >95% in the BPK mice (0.04±0.02 pmoles/min/mg protein; n=3), and there was no apparent inhibition of HET-0016 on any of the other metabolites of arachidonic acid formed by the kidney (FIG. 6B).

Molecular determination of the cytochrome P450 4A isoforms in the conditionally immortalized renal epithelial cells isolated from non-cystic Balb/C and cystic BPK mouse kidneys: To determine which CYP isoforms are expressed and may contribute to the formation of 20-HETE in cystic epithelial cells, we designed specific PCR primers to determine whether the cytochrome P450 4A and 4F isoforms would be differentially expressed in cystic BPK versus non-cystic Balb/C epithelial cells (Table 4). We designed an in vitro experiment to determine the potential role of Cyp4a12 in cellular proliferation by genetically modifying conditionally immortalized renal epithelial cells isolated from the intercrossed BPK X ImmortoMouse as described by Sweeney W E et al. *Am J Physiol Cell Physiol*, 281:C1695-705, 2001.

These conditionally immortalized epithelial cells contained a thermo-labile mutant of the SV40 large T antigen under the control of an interferon-γinducible promoter (H-2 K$^b$) (Jat P S et al. *Proc Natl Acad Sci USA*, 88:5096-100, 1991). This permitted control of the large T antigen levels, and allows for the switching of the cells from permissive to non-permissive culture conditions (Takacs-Jarrett M et al. *Am J Physiol Cell Physiol*, 280:C228-36, 2001). The cells were placed under non-permissive conditions for at least 6 days to minimize the expression of the T-antigen prior to the harvesting of the total RNA for analysis.

TABLE 4 mRNA levels of cytochrome P450 4A isoforms: RT-real-time PCR results demonstrating the steady state levels of CYP4A isoforms in the cystic BPK and non-cystic Balb/C cells. The cells were harvested 10 days after culturing under non-permissive conditions, and total RNA was extracted using TRIzol reagent. RT-PCR was performed using specific primers against the murine Cyp4a10, Cyp4a12 and Cyp4a14 genetic sequence.

| Gene | Non-cystic Balb/C cells (copies/μg RNA) | Cystic BPK cells (copies/μg RNA) |
|---|---|---|
| Cyp4a10 | 158.2 +/− 35.5 (n = 4) | 595.3 +/− 252.5 (n = 5) |
| Cyp4a12 | 43,664 +/− 32,171 (n = 4) | 369,053 +/− 40,177* (n = 5) |
| Cyp4a14 | UND (n = 4) | UND (n = 4) |

*P<0.001 difference in the levels of Cyp4a12 mRNA between cystic BPK versus non-cystic Balb/C cells.
UND = undetectable.

From our analysis, we found that there were low level steady state levels of Cyp4a10 mRNA in the non-cystic Balb/C cells (158.2±35.5 copies/μg RNA; mean±SEM; n=4) with a slight, non-significant increase (P>0.05) in the cystic BPK cells (595.3±252.5 copies/μg RNA; n=5). For the Cyp4a12 mRNA, the steady state levels in Balb/C cells were 43,664±32,171 copies/μg RNA (n=4), which was significantly higher (P<0.001) than the Cyp4a10 mRNA levels in either BPK or Balb/C cells (n=4-5). Interestingly, the Cyp4a12 mRNA in the cystic BPK cells was about 10-fold higher (P<0.001) at 369,053±40,177 copies/μg RNA (n=5). No detectable copies of Cyp4a14 mRNA was detected in either the BPK or Balb/C cells (n=4/cell line). From our RT-PCR results, the increased steady state levels of both Cyp4a10 and Cyp4a12 isoforms indicated a potential biological role in mediating epithelial cell proliferation.

Genetic Modification of Conditionally Immortalized Renal Epithelial Cells Using VSV-G Pseudotyped Lentiviral Vectors:

Full-length Cyp4a10 and Cyp4a12 cDNA driven by the human ubiquitin C promoter were cloned into modified lentiviral vector transfer plasmids as described by Park F et al. (*Mol Ther*, 4:164-73, 2001) and shown in a schematic in FIG. 3. Lentiviral vectors were generated and serially transduced into non-permissive Balb/C epithelial cells at a MOI about 40. As shown by the FACS analysis, all of the cells transduced by the lentiviral vectors expressed the EGFP transgene (FIG. 7A) and no spurious fluorescence was noted in any of the vehicle-treated non-cystic Balb/C cells or both of the lentiviral vector-transduced Balb/C cells expressing the CYP4A isoforms.

Figure 7:
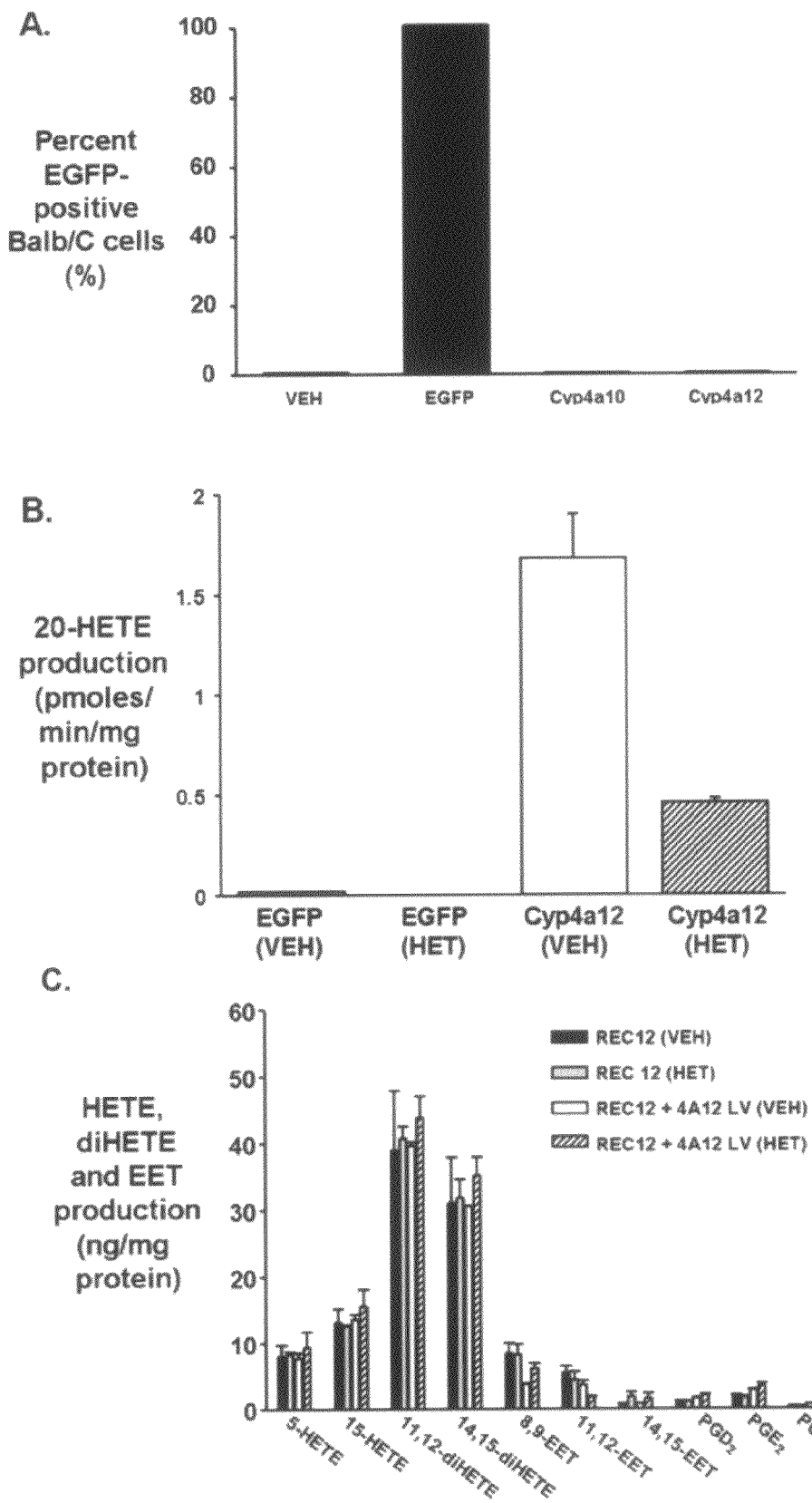
FIG. 7 shows transduction efficiency and transgene expression and function following genetic manipulation using lentiviral vectors on conditionally immortalized murine renal epithelial cells. (A) Histogram analysis following FACS analysis demonstrating the fluorescence intensity of a representative group of lentiviral vector-transduced non-cystic Balb/C (+/+) cells with either vehicle, EGFP, Cyp4a10 or Cyp4a12. (B) Graphical analysis of the transduction efficiency of non-cystic renal epithelial cells using lentiviral vectors. (C) Functional analysis of 20-HETE production using the lentiviral vector-treated non-cystic Balb/C (+/+) cells. * $P<0.001$ difference between Cyp4a12 versus non-cystic Balb/C cells treated with vehicle (VEH) or HET-0016 (HET). CTRL=vehicle-treatment; GFP=cells transduced with lentiviral vectors expressing EGFP (GFP), Cyp4a10 and Cyp4a12; HET=HET-0016 (10 μM).

The functional activity of the cytochrome P450 4A isoforms was determined using liquid chromatography coupled to mass spectrometry in the 20-HETE production assay (FIG. 7B). This showed that the 20-HETE production was significantly higher (P<0.001) in the Cyp4a12 expressing cells (n=3) compared to the untreated EGFP-expressing Balb/C cells (n=4). Similar increases in 20-HETE production were observed using Cyp4a10 transduced Balb/C cells and this was correlated to increased protein detection of Cyp4a10 by Western blot analysis (data not shown). In addition, the lentiviral vector-mediated over-expression of Cyp4a12 to synthesize 20-HETE could be markedly inhibited by >70% (n=2) following administration of HET-0016 at a dose of 1 μM during the 20-HETE production assay. No significant differences were noted in the production of any of the other HETEs, diHETEs or EETs using the over-expressing Cyp4a12 compared to the untreated Balb/C cells (FIG. 7C). These experiments demonstrated that we were able to highly manipulate the murine renal epithelial cells in vitro to produce specific isoforms of the CYP4A family.

Effect of 20-HETE Over-Production on Cell Proliferation in Non-Cystic Balb/C and Cystic BPK Renal Epithelial Cells:

The cells in this experiment were transduced using the lentiviral vectors in the presence of γ-IFN (i.e., permissive state) and allowed to expand. Once the cells were expanded, the transduced cells were grown in the absence of γ-IFN (i.e., non-permissive state) for 10 days. The cells were harvested and counted to initiate the proliferation experiment.

Figure 8:
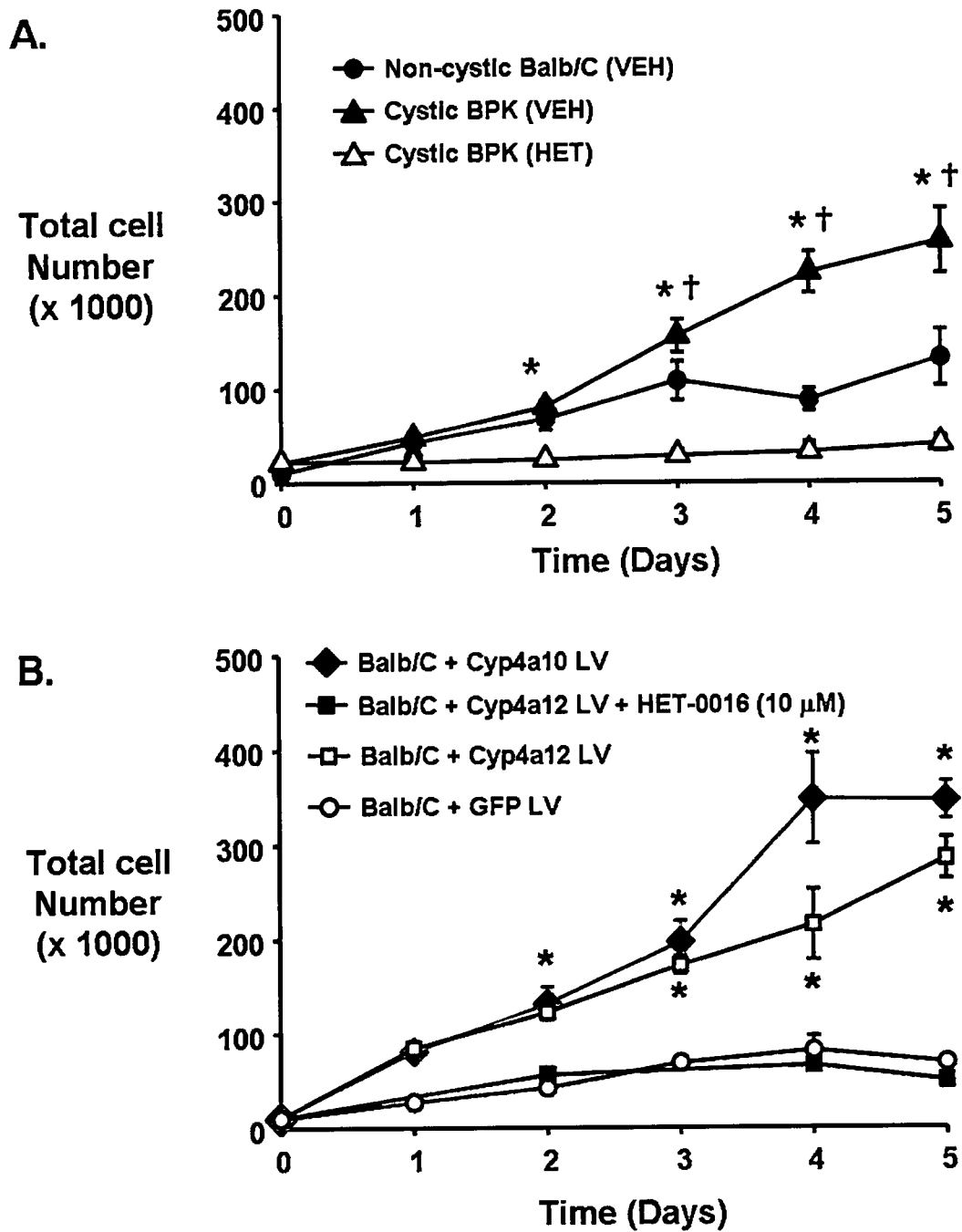
FIG. 8 shows the cell number in cystic BPK and non-cystic Balb/C (+/+) renal epithelial cells. (A) Cystic BPK and non-cystic Balb/C renal epithelial cells were incubated in serum-free media without γ-IFN at a temperature of 37° C. (non-permissive conditions) for a period of 6 days. At this point, the BPK (▲) and Balb/C (O) cells were plated into individual wells and the cells were counted daily by hemocytometry over a 5-day period. For the 20-HETE synthesis inhibition group, HET-0016 (10 μM) was added to the media on a daily basis (Δ). n=4-6 wells/cell line. * $P<0.001$ difference between BPK cells treated with VEH versus HET. † $P<0.001$ difference between BPK (VEH) versus Balb/C. (B) Non-cystic Balb/C renal epithelial cells were serially transduced on a daily basis with lentiviral vectors expressing EGFP (O), Cyp4a10 (♦) and Cyp4a12 (□) under permissive conditions (in the presence of γ-IFN at 33° C.). The cells were expanded and placed in non-permissive conditions for a period of 6 days. At this point, the cells were plated into individual wells and the cells were counted on a daily basis using a hemocytometer for a 5-day period (n=4-6 wells/time point). HET-0016 (10 μM) was added to the media with the cells transduced with the Cyp4a12-expressing lentiviral vector (■; n=3-6 wells/time point). * $P<0.001$ difference between CYP4A-transduced Balb/C cells compared to EGFP-transduced Balb/C cells.
Figure 9:
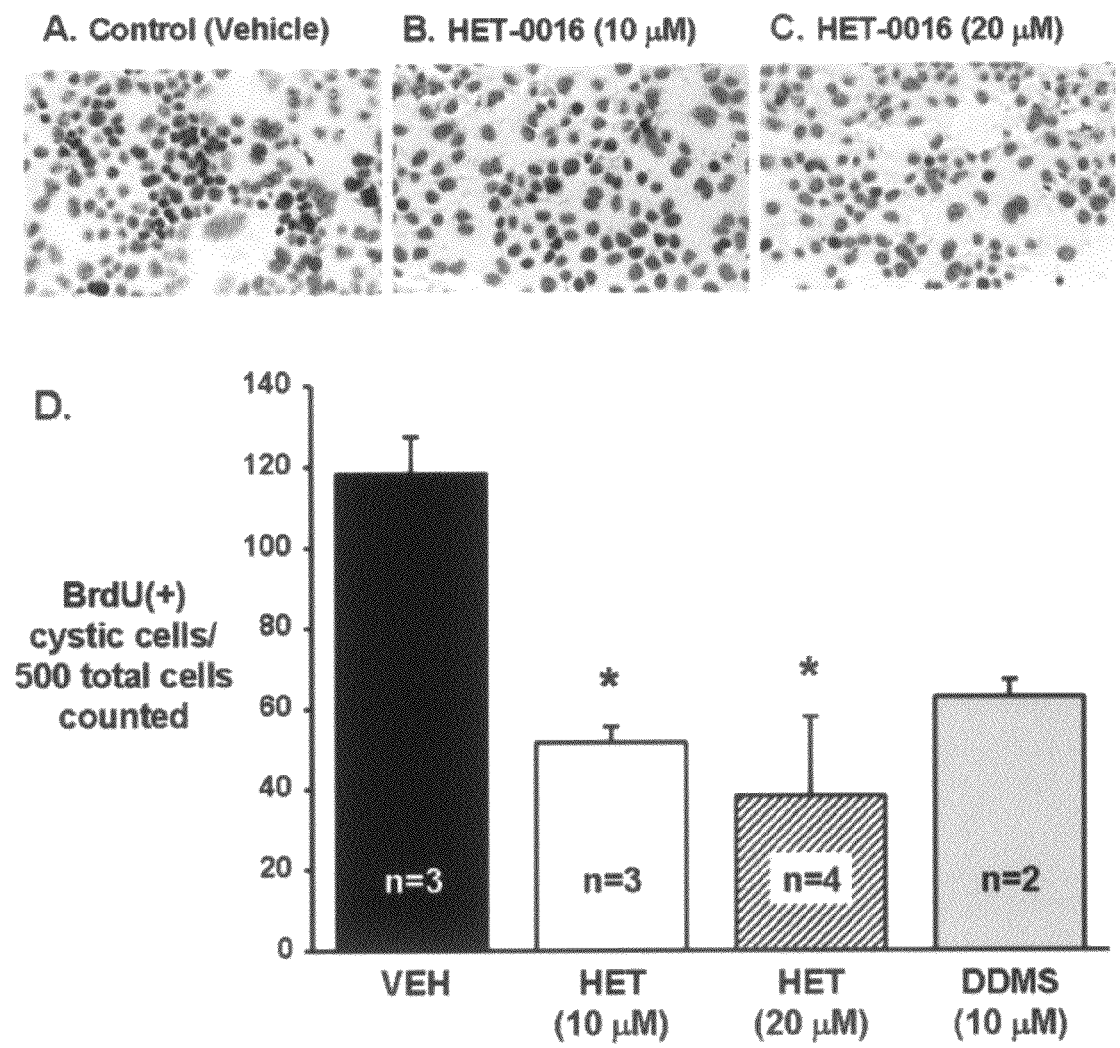
FIG. 9 shows decreased cell cycle progression in cystic BPK cells in the presence of 20-HETE synthesis inhibitors. Cystic BPK cells were incubated in serum-free media without γ-IFN at a temperature of 37° C. (non-permissive conditions) for a period of 10 days, and then incubated in the presence of vehicle (A) or two chemically dissimilar 20-HETE synthesis inhibitors, HET-0016 (10 and 20 µM; B and C) and DDMS (10 µM; D) for a period of 36 hours. 5-bromo-2'-deoxyuridine (BrdU), which is a marker for DNA synthesis, was added at a concentration of 30 µM for 3 hours prior to the end of the experiment. Cells were methanol-fixed, and cellular uptake of BrdU was identified by immunohistology with biotinylated monoclonal anti-BrdU antibody. (D) Graphic representation of the data expressing the number of BrdU-labeled cells per 500 total cells counted. n=2-4 samples/group. * P<0.05 difference between HET-0016 versus vehicle-treated REC11 cells.

Under the non-permissive conditions, cystic BPK cells were significantly increased (P<0.001) in cell number to 256,700±17,136 (n=4) by day 3 relative to the non-cystic Balb/C cells (132,892±11,925; n=6) over the 5-day experiment (FIG. 8A). In the presence of a 20-HETE synthesis inhibitor, HET-0016 (10 μM), the number of cystic BPK cells were significantly reduced (P<0.001) to 40,744±4,322 (n=4) by day 2 compared to the vehicle-treated BPK cells. The decreased total number of REC11 cells in the presence of HET-0016 was consistent with the 5-bromo-2'-deoxyuridine (BrdU) incorporation experiment (FIG. 9), which provides an index of DNA synthesis, where incubation of the BPK cells with HET-0016 (10 and 20 μM) resulted in significantly lower (P<0.001) BrdU-positive cells [52 and 38 BrdU(+) cells] compared to the vehicle-treated BPK cells [118 BrdU(+) cells]. Blockade with an alternate inhibitor of 20-HETE synthesis, DDMS, resulted in a similar decrease in the number of BrdU-positive cystic BPK cells to 63 (n=2) compared to vehicle treatment. Overall, these in vitro experiments demonstrate that 20-HETE mediates the proliferative activity of the cystic BPK cells.

The total number of non-cystic Balb/C cells were significantly increased (p<0.001) following transduction with either Cyp4a10 (347,075±19,635; n=4) or Cyp4a12 (285,792±21,892; n=6) compared to the EGFP-transduced Balb/C cells (68,767±4,124; n=6) by day 3 of the experiment (FIG. 8B). This demonstrates that the non-cystic Balb/C cells could be modified to simulate the proliferative phenotype of the cystic BPK cells by over-expression of Cyp4a10 and Cyp4a12. Moreover, blockade in the production of 20-HETE using HET-0016 (10 μM), dramatically reduced the number of Cyp4a12-expressing Balb/C cells (49,700±5,085; n=3). There was no significant difference (P>0.05) between Balb/C cells treated with vehicle or the EGFP-transduced lentiviral vectors.

EXAMPLE 4

Figure 10:
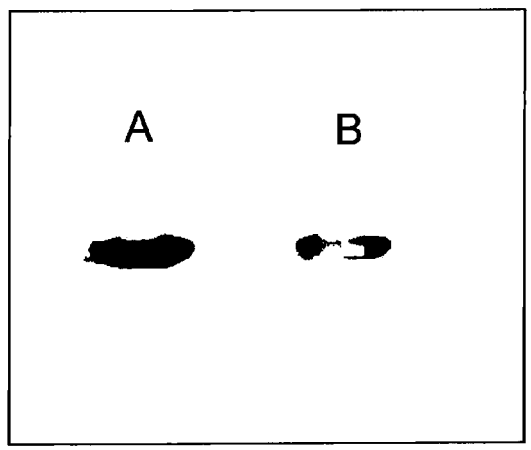
FIG. 10 shows the effect of chronic HET0016 treatment on EGFR phosphorylation in the kidney of BPK mice.
Figure 10:
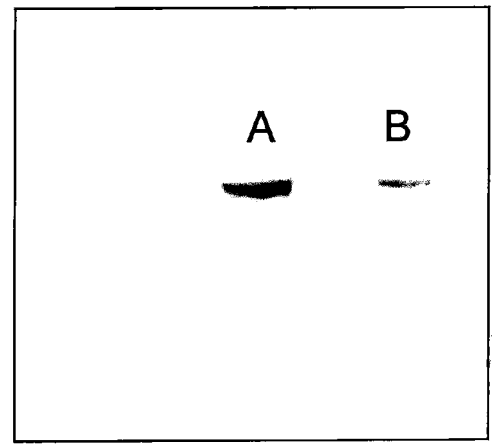

Effect of Chronic HET0016 Treatment on EGFR Phosphorylation in the Kidney of BPK Mice The BPK model, a murine model of ARPKD, arose as a spontaneous mutation in an inbred colony of Balb/c mice and has been extensively characterized (Nauta J et al. Pediatr Nephrol 1993, 7:163-72; Nauta J et al. Pediatr Res 1995, 37:755-63; and Sweeney W E et al. Kidney Int 2003, 64:1310-9). Affected animals die at postnatal day (PN) 24 (average) with a range of PN-21 to PN-29 days. Extrarenal manifestations include biliary proliferation and ductal ectasia (BDE). Balb/c controls were utilized in all experiments. All animal experiments were conducted in accordance with policies of the NIH Guide for the Care and Use of Laboratory Animals and the Institutional Animal Care and Use Committee (IACUC) of the Medical College of Wisconsin. Western blot analysis of EGFR phosphorylation was conducted for BPK renal tissues following 13 days (PN-7 to PN-20) of treatment with vehicle (ip) (lane A of FIG. 10) or HET0016 (ip, 10 mg/Kg/day) (lane B or FIG. 10). As shown in FIG. 10 with two separate experiments (Group 1 and Group 2), HET0016 reduced the phosphorylation (activation) of EGFR in the renal tissue (in the medulla region of kidney) from the cystic animal. The reduced phosphorylation of the EGFR directly correlates with the reduced size of the HET0016-treated cystic kidney, reduced KW/BW ratio, and improved morphology of the HET0016-treated cystic kidney observed in the immunohistochemistry study described above in Example 3.

EXAMPLE 5

Effect of HET0016 on the Proliferation of Primary Collecting Tubular Cystic Cells Obtained from a PCK Rat The PCK (polycystic kidney) rats were established in 2000 from a Crj:CD/SD animal that developed a spontaneous mutation resulting in renal and hepatic abnormalities. PCK rats exhibit multiorgan cyst pathology similar to human ARPKD. These rats develop collecting duct derived renal cysts, and multiple segmental and saccular dilatations of intrahepatic bile ducts due to ductal plate malformation, as well as progressive portal fibrosis (Lager D J et al. Kidney Int 2001, 59:126-36). Linkage and gene cloning analysis demonstrated that the kidney and liver disease in PCK rats and in ARPKD patients is caused by mutations to orthologous genes, PKHD1/Pkhd1 (Ward C J et al. Nat Genet 2002, 30:259-69).

Renal CT cells from the PCK rat were isolated as described in Sweeney W. E. et al., Am J Physiol C Physiol, 2001, 281:C1695-705, using monoclonal F-13 a principal cells specific surface marker (Fejes-Toth N et al., J Tiss Cult Meth 1991, 13:179-184).

To determine the level of proliferation in the cystic PCK CT cells, the cells were incubated with HET-0016 (10 µM) or vehicle for 36 hours. Three hours prior to the harvesting of the cells, 5-bromo-2'-deoxyuridine (BrdU) at a concentration of 30 µM was added to determine the level of cell cycle inhibition. The cells were subsequently methanol fixed and BrdU-positive cells were identified by immunohistology with biotinylated monoclonal anti-BrdU antibody (Zymed, South San Francisco, Calif.). Data were expressed as the percentage of BrdU-labeled cells per 500 counted cells. In the vehicle treated group, 28.5%±1% (n=3) were labeled with BrdU. In the HET-0016 treated group, 10.8%±1% (n=3) were labeled with BrdU. This data demonstrates that HET-0016 reduces the proliferation of cystic epithelial cells isolated from the rat model of human ARPKD.

EXAMPLE 6

Effect of Chronic HET0016 Treatment on Kidney Weight to Body Weight (KW/BW) and Liver Weight to Body Weight (LW/BW) in PCK Rats PCK rats, an orthologous model of human ARPKD (PKHD1), received daily IP injections of vehicle or HET0016 at 10 mg/kg/daily, starting at postnatal day 7 (PN-7). Animals were treated daily from PN-7 to PN-55 (48 doses). Kidney and liver were harvested at PN-55.

As shown in Table 5, HET0016 treatment resulted in a 14% decrease in total body weight but a 23% decrease in KW/BW ratio and a 25% decrease in LW/BW ratio. The fact that kidney and liver weight decreased to a greater extent than total body weight supports that HET0016 reduced both renal and hepatic cyst formation in this animal model of human ARPKD.

TABLE 5

|  | BW | KW (% BW) | LW (% BW) |
|---|---|---|---|
| Vehicle | 108 | 1.26 | 5.7 |
| HET0016 | 93 | 0.97 | 4.3 |

Figure 11:
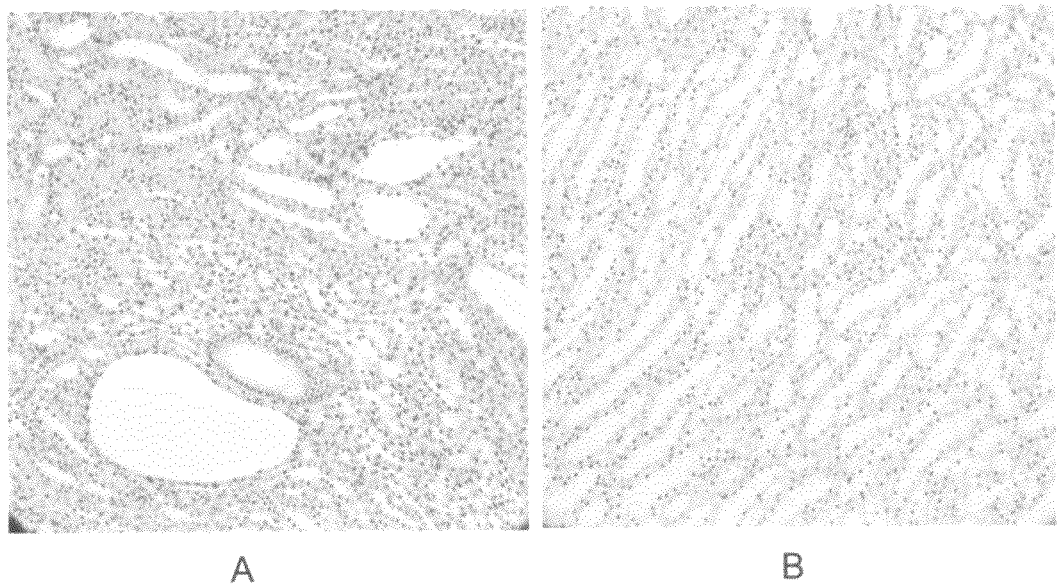
FIG. 11 shows renal morphology of the kidney of PCK rat treated with vehicle (panel A) or HET-0016 (10 mg/kg/day, IP) (panel B) from postnatal day 7 through day 55. The data demonstrates a dramatic reduction in cyst size and tubular epithelial proliferation in the rat treated with HET0016 (original mag.=20×).
Figure 12:
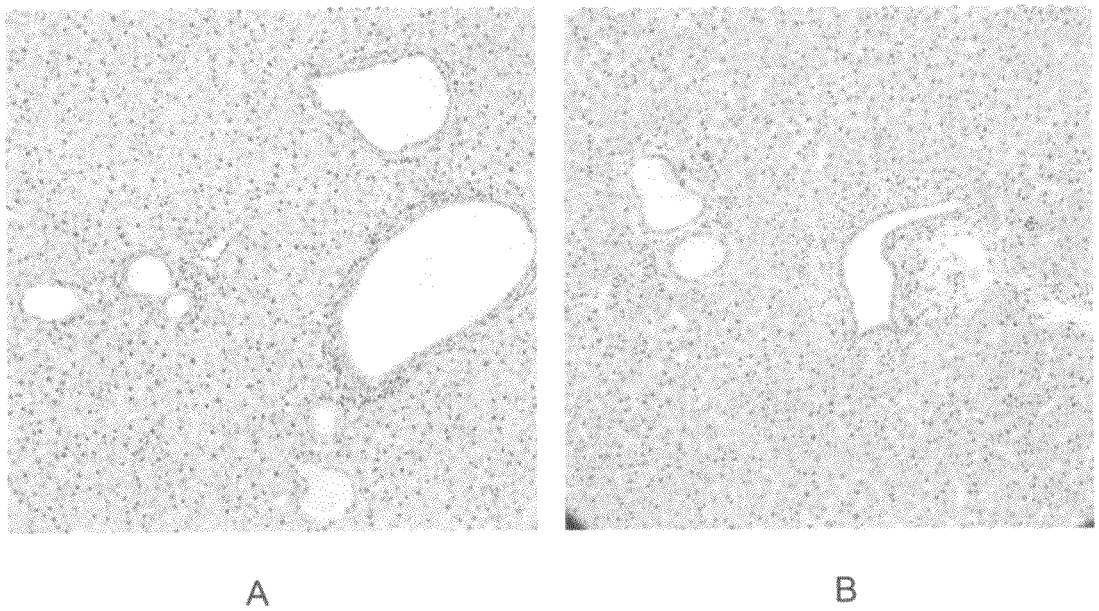
FIG. 12 shows the histology of the liver of a PCK rat treated with vehicle (panel A) or HET-0016 (10 mg/kg/day IP) (panel B) from post natal day 7 through day 55 (panel B). The data demonstrate a dramatic reduction in the size and number of biliary cysts and in the proliferation of biliary epithelial cells in the rats treated with HET0016 (original mag.=20×).

Morphologies of the vehicle- and HET0016-treated rat kidneys and livers were also compared. We observed a dramatic reduction in size and number of cysts and tubular epithelial proliferation in the kidneys of the rats treated with HET0016 (FIG. 11). Similarly, we observed a dramatic reduction in size and number of cysts and reduced biliary epithelial proliferation in the liver of the rats treated with HET0016 (FIG. 12).

The present invention is not intended to be limited to the foregoing examples, but encompasses all such modifications and variations as come within the scope of the appended claims.

We claim:

1. A method for treating a disease in a mammal in need thereof wherein the disease is selected from autosomal recessive polycystic kidney disease (ARPKD), ARPKD associated congenital hepatic fibrosis, and ARPKD associated Caroli's disease, the method comprising the step of:
    administering an agent selected from a 20-hydroxyeicosatetraenoic acid (20-HETE) synthesizing enzyme inhibitor and a 20-HETE antagonist to the mammal in an amount sufficient to prevent or treat the disease.

2. The method of claim 1, wherein the disease is ARPKD.

3. The method of claim 1, wherein the mammal is human.

4. The method of claim 1 further comprising the step of: observing improvement in the mammal having the disease.

5. The method of claim 1, wherein the agent is a 20-HETE synthesizing enzyme inhibitor.

6. The method of claim 5, wherein the 20-HETE synthesizing enzyme inhibitor is selected from N-hydroxy-N'-(4-n-butyl-2-methylphenyl)-formamidine (HET0016) and N-(3-Chloro-4-morpholin-4-yl)phenyl-N'-hydroxyimidoformamide (TS-011).

7. The method of claim 5, wherein the 20-HETE synthesizing enzyme inhibitor is selected from a class I hydroxyformamidine compound 20-HETE synthesis inhibitor.

8. The method of claim 5, wherein the 20-HETE synthesizing enzyme inhibitor is selected from a class II hydroxyformamidine compound 20-HETE synthesis inhibitor.

9. The method of claim 5, wherein the 20-HETE synthesizing enzyme inhibitor is selected from a class III hydroxyformamidine compound 20-HETE synthesis inhibitor.

10. The method of claim 5, wherein the 20-HETE synthesizing enzyme inhibitor is selected from an imidazole derivative 20-HETE synthesis inhibitor.

11. The method of claim 5, wherein the 20-HETE synthesizing enzyme inhibitor is selected from a pyrazole derivative 20-HETE synthesis inhibitor.

12. The method of claim 5, wherein the 20-HETE synthesizing enzyme inhibitor is selected from an isoxazole derivative 20-HETE synthesis inhibitor.

13. The method of claim 1, wherein the agent is a 20-HETE antagonist.

* * * * *

SEQUENCE LISTING

<160> NUMBER OF SEQ ID NOS: 6

<210> SEQ ID NO 1
<211> LENGTH: 22
<212> TYPE: DNA
<213> ORGANISM: Artificial
<220> FEATURE:
<223> OTHER INFORMATION: Synthetic oligonucleotide

<400> SEQUENCE: 1
gacaaggacc tacgtgctga gg                                    22

<210> SEQ ID NO 2
<211> LENGTH: 21

```
<212> TYPE: DNA
<213> ORGANISM: Artificial
<220> FEATURE:
<223> OTHER INFORMATION: Synthetic oligonucleotide

<400> SEQUENCE: 2
ctcatagcaa attgtttccc a                                              21

<210> SEQ ID NO 3
<211> LENGTH: 21
<212> TYPE: DNA
<213> ORGANISM: Artificial
<220> FEATURE:
<223> OTHER INFORMATION: Synthetic oligonucleotide

<400> SEQUENCE: 3
tgagtcctat gaaagagtgc c                                              21

<210> SEQ ID NO 4
<211> LENGTH: 21
<212> TYPE: DNA
<213> ORGANISM: Artificial
<220> FEATURE:
<223> OTHER INFORMATION: Synthetic oligonucleotide

<400> SEQUENCE: 4
ctggaagccc agcagaaggt g                                              21

<210> SEQ ID NO 5
<211> LENGTH: 21
<212> TYPE: DNA
<213> ORGANISM: Artificial
<220> FEATURE:
<223> OTHER INFORMATION: Synthetic oligonucleotide

<400> SEQUENCE: 5
cctacaaggt acttggatgg t                                              21

<210> SEQ ID NO 6
<211> LENGTH: 22
<212> TYPE: DNA
<213> ORGANISM: Artificial
<220> FEATURE:
<223> OTHER INFORMATION: Synthetic oliognucleotide

<400> SEQUENCE: 6
atcataaagc aggactcgta ta                                             22
```